(12) United States Patent
Kishimoto et al.

(10) Patent No.: US 9,990,465 B2
(45) Date of Patent: Jun. 5, 2018

(54) INFORMATION PROCESSING DEVICE, INFORMATION PROCESSING SYSTEM, AND INFORMATION PROCESSING METHOD

(71) Applicants: Yuka Kishimoto, Tokyo (JP); Sadayuki Ohsawa, Tokyo (JP); Nobuhisa Kawakami, Kanagawa (JP)

(72) Inventors: Yuka Kishimoto, Tokyo (JP); Sadayuki Ohsawa, Tokyo (JP); Nobuhisa Kawakami, Kanagawa (JP)

(73) Assignee: RICOH COMPANY, LTD., Tokyo (JP)

( * ) Notice: Subject to any disclaimer, the term of this patent is extended or adjusted under 35 U.S.C. 154(b) by 0 days. days.

(21) Appl. No.: 15/461,531

(22) Filed: Mar. 17, 2017

(65) Prior Publication Data

US 2017/0270248 A1 Sep. 21, 2017

(30) Foreign Application Priority Data

Mar. 18, 2016 (JP) ................................ 2016-056320

(51) Int. Cl.
*G06F 19/00* (2018.01)
*G06Q 10/10* (2012.01)
*H04N 1/00* (2006.01)

(52) U.S. Cl.
CPC ........... *G06F 19/321* (2013.01); *G06Q 10/10* (2013.01); *G16H 10/60* (2018.01); *H04N 1/00018* (2013.01); *H04N 1/00413* (2013.01)

(58) Field of Classification Search
CPC .... G06F 19/322; G06F 19/327; G06F 19/328; G06F 19/3487; G06Q 10/10;
(Continued)

(56) References Cited

U.S. PATENT DOCUMENTS 5,832,450 A * 11/1998 Myers ................... G06F 19/363
705/3
5,933,809 A * 8/1999 Hunt ...................... G06Q 30/04
705/2

(Continued)

FOREIGN PATENT DOCUMENTS

JP 2003-248722 9/2003
JP 2009-205477 9/2009

*Primary Examiner* — Negussie Worku
(74) *Attorney, Agent, or Firm* — Harness, Dickey & Pierce, P.L.C.

(57) ABSTRACT

An information processing device is configured to keep image data of paper document in association with first identification information, display a selection list from which one or more pieces of identification information including at least the first identification information is able to be selected, display a list of image data associated with one piece of identification information selected from the selection list in a specified list-display area of a plurality of list-display areas, and change, in response to reception of an operation of moving image data specified from the list of image data displayed in the specified list-display area, to another list-display area in a state in which a list of the image data associated with another piece of identification information selected from the selection list is displayed in the other list-display area, a keeping destination of the specified image data to the other piece of identification information.

16 Claims, 18 Drawing Sheets

(58) Field of Classification Search
CPC ........ G06Q 50/22; G06Q 50/24; H04L 67/10;
H04L 67/18; H04L 67/2823; H04L 67/32
USPC .............................. 709/229; 705/3; 713/171
See application file for complete search history.

(56) References Cited

U.S. PATENT DOCUMENTS

| | | | |
|---|---|---|---|
| 8,391,583 B1* | 3/2013 | Mennie | G06K 9/03 |
| | | | 209/534 |
| 8,417,017 B1* | 4/2013 | Beutel | G06Q 20/042 |
| | | | 340/5.86 |
| 8,627,939 B1* | 1/2014 | Jones | G07F 19/20 |
| | | | 194/207 |
| 2008/0158597 A1* | 7/2008 | Hashimoto | G06F 21/608 |
| | | | 358/1.15 |
| 2010/0067035 A1* | 3/2010 | Kawakubo | H04N 1/00222 |
| | | | 358/1.13 |
| 2012/0124252 A1* | 5/2012 | Kayama | G06F 13/4282 |
| | | | 710/32 |
| 2012/0194700 A1* | 8/2012 | Ebata | G06K 9/00288 |
| | | | 348/231.3 |
| 2013/0159021 A1* | 6/2013 | Felsher | G06F 19/322 |
| | | | 705/3 |
| 2016/0125165 A1* | 5/2016 | Kelly | G06F 17/30864 |
| | | | 705/2 |
| 2016/0239697 A1* | 8/2016 | Nozaka | G06Q 10/06 |
| 2017/0004593 A1* | 1/2017 | Toshimitsu | G06Q 50/22 |
| 2017/0013152 A1* | 1/2017 | Morii | H04N 1/00862 |
| 2017/0171399 A1* | 6/2017 | Yamada | G06F 3/1207 |

* cited by examiner

FIG.2

| PATIENT ID: 1000101 | | | | | | |
|---|---|---|---|---|---|---|
| | 2015/07/13 | 2015/07/18 | 2015/07/17 | 2015/07/22 | 2015/08/12 | |
| MEDICAL RECORD | | | | FIRST MEDICAL RECORD | SECOND MEDICAL RECORD | |
| EXAMINATION REPORT | | | EXAMINATION REPORT | | | |
| MEDICAL INTERVIEW SHEET | | | | | | |
| REFERRAL LETTER | REFERRAL LETTER FROM HOSPITAL A | | | | | |
| MEDICAL CERTIFICATE | | | MEDICAL CERTIFICATE | | | |
| EXPLANATION AND CONSENT FORM | | | | | | |

| PATIENT ID: 1000101 | | | | | | |
|---|---|---|---|---|---|---|
| | 2015/07/13 | 2015/07/18 | 2015/07/17 | 2015/07/22 | 2015/08/12 | 2015/08/17 |
| MEDICAL RECORD | | | | ▨ FIRST MEDICAL RECORD | ▨ SECOND MEDICAL RECORD | |
| EXAMINATION REPORT | | | ▨ EXAMINATION REPORT | | | |
| MEDICAL INTERVIEW SHEET | | | | | | |
| REFERRAL LETTER | ▨ REFERRAL LETTER FROM HOSPITAL A | | | | | |
| MEDICAL CERTIFICATE | | ▨ MEDICAL CERTIFICATE | | | | |
| EXPLANATION AND CONSENT FORM | | | | | | ▨ EXPLANATION AND CONSENT FORM |

11

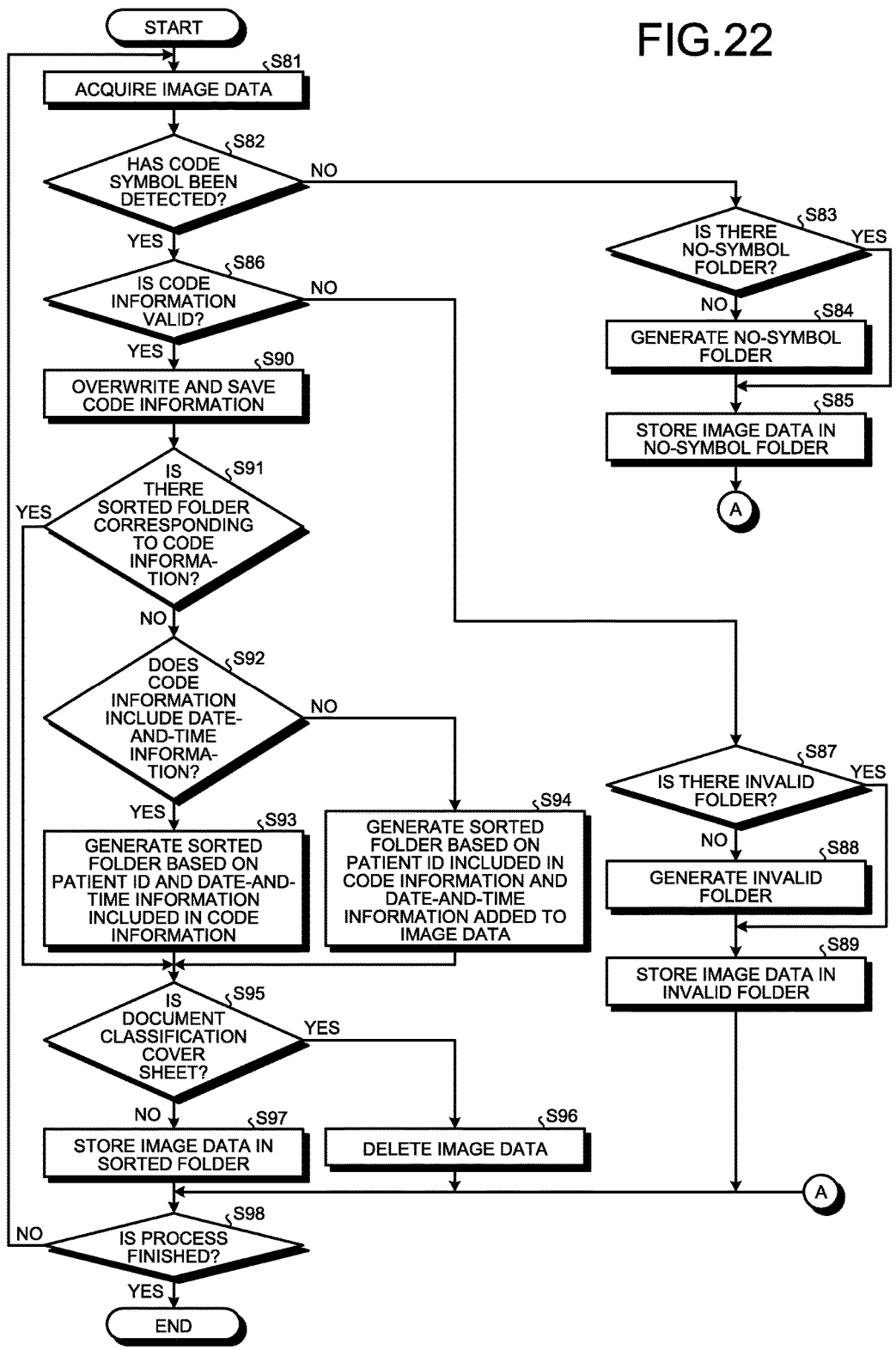

INFORMATION PROCESSING DEVICE, INFORMATION PROCESSING SYSTEM, AND INFORMATION PROCESSING METHOD

CROSS-REFERENCE TO RELATED APPLICATIONS

The present application claims priority under 35 U.S.C. § 119 to Japanese Patent Application No. 2016-056320, filed on Mar. 18, 2016. The contents of which are incorporated herein by reference in their entirety.

BACKGROUND OF THE INVENTION

1. Field of the Invention

The present invention relates to an information processing device, an information processing system, and an information processing method.

2. Description of the Related Art

In recent years, paper documents are computerized in various fields in order to unitarily manage or share information. In general, computerization is performed by reading paper documents by a scanner device. Electronic data generated by computerization is sorted in accordance with the attribute of the original paper document and is registered into a database or the like to be shared.

For example, at a medical site such as a hospital, medical staff such as a doctor, a nurse, or clerical staff performs computerizing work on a paper document of a patient, sorts generated electronic data for each patient, and thereafter registers the electronic data into a database, for example, an electronic medical record system. Conventionally, a technique has been proposed in which identification information for identifying a patient is printed on a paper document in advance, and document data is stored in association with the document data with electronic medical records of a corresponding patient using the identification information read during computerization (for example, Japanese Patent Application Laid-open No. 2009-205477).

However, the conventional technique described above is premised on that identification information is included in all the paper documents. Therefore, it is difficult to apply the conventional technique to a paper document not including identification information. For example, a referral letter used at a medical site is a paper document brought from another medical institution, and therefore the referral letter does not include valid identification information in general. In a case where a paper document not including identification information is mixed as described above, there is conventionally a possibility that registration is performed while appropriate sorting cannot be performed. Also, according to the conventional technique, it is impossible to check whether electronic data is to be registered. Therefore, there is still room for improvement with regard to convenience.

SUMMARY OF THE INVENTION

According to one aspect of the present invention, an information processing device is configured to process image data of a paper document read by a scanner. The information processing device includes a keeping unit, a detection unit, a first sorting unit, a first display unit, a second display unit, a reception unit, a changing unit, and a registration unit. The keeping unit is configured to keep image data of the paper document in units of a read page in association with first identification information. The detection unit is configured to detect first identification information included in the paper document from the image data of the paper document. The first sorting unit is configured to keep the image data of non-detection from which the first identification information has not been detected by the detection unit, in the keeping unit in association with the first identification information detected lastly. The first display unit is configured to display a selection list from which one or more pieces of identification information including at least the first identification information associated with the image data kept in the keeping unit, is able to be selected. The second display unit is configured to display a list of image data associated with one piece of identification information selected from the selection list in a specified list-display area of a plurality of list-display areas in each of which a list of image data is to be displayed. The reception unit is configured to receive an operation of moving image data specified from the list of image data displayed in the specified list-display area, to another list-display area. The changing unit is configured to change, in response to reception of the operation by the reception unit in a state in which a list of the image data associated with another piece of identification information selected from the selection list is displayed in the other list-display area, a keeping destination of the specified image data to the other piece of identification information. The registration unit configured to register the image data associated with the first identification information in units of the first identification information kept by the keeping unit, in an external device.

BRIEF DESCRIPTION OF THE DRAWINGS

FIG. 2 is a diagram illustrating an example of document data stored and managed by a database;

FIG. 20 is a diagram illustrating another example of document data stored and managed by the database;

FIG. 22 is a flowchart illustrating another example of the sorting process performed by the sorting processing device.

The accompanying drawings are intended to depict exemplary embodiments of the present invention and should not be interpreted to limit the scope thereof. Identical or similar reference numerals designate identical or similar components throughout the various drawings.

DESCRIPTION OF THE EMBODIMENTS

Figure 1:
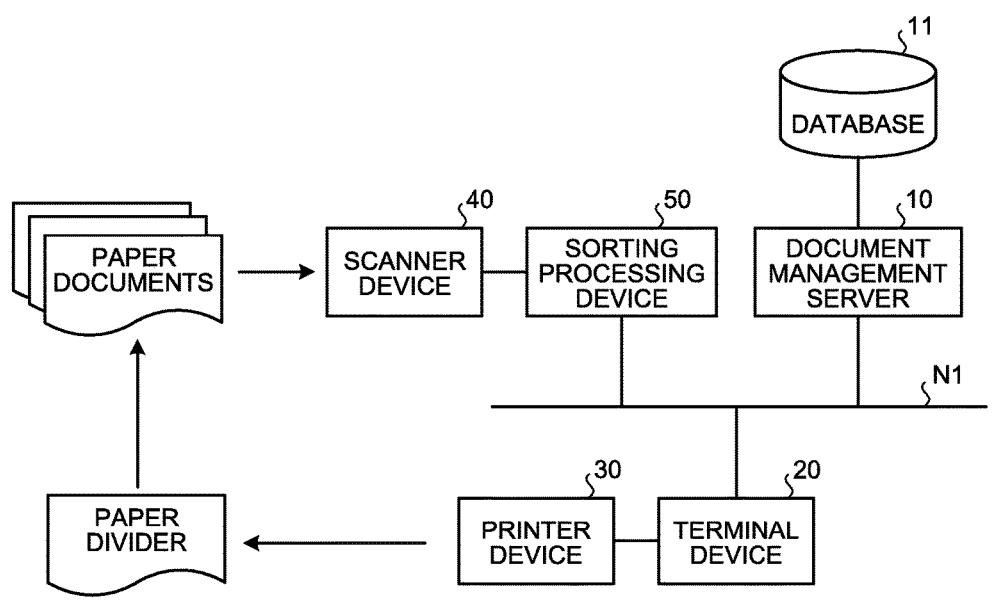
FIG. 1 is a diagram illustrating a configuration example of an information processing system according to a present embodiment.

The terminology used herein is for the purpose of describing particular embodiments only and is not intended to be limiting of the present invention.

As used herein, the singular forms "a", "an" and "the" are intended to include the plural forms as well, unless the context clearly indicates otherwise.

In describing preferred embodiments illustrated in the drawings, specific terminology may be employed for the sake of clarity. However, the disclosure of this patent specification is not intended to be limited to the specific terminology so selected, and it is to be understood that each specific element includes all technical equivalents that have the same function, operate in a similar manner, and achieve a similar result.

Embodiments of an information processing device, an information processing system, and an information processing method according to the present invention will be explained in detail below with reference to the accompanying drawings. In the following embodiments, while the present invention is applied to a medial site such as a hospital as an example, the present invention is not limited by the embodiments.

An embodiment has an object to improve convenience related to sorting of computerized paper documents in an environment in which both a paper document including identification information for sorting and a paper document not including the identification information are mixed.

Information Processing System

FIG. 1 is a diagram illustrating a configuration example of an information processing system according to a present embodiment. As illustrated in FIG. 1, a document management system includes a document management server 10, a terminal device 20, a printer device 30, a scanner device 40, and a sorting processing device 50.

The document management server 10 is, for example, a server device and is connected to the terminal device 20 and the sorting processing device 50 via a network N1 such as a LAN (Local Area Network), in a communicable manner. The document management server 10 includes a database 11 as a storage and management unit for unitarily storing and managing various types of information related to this system.

The database 11 stores and manages staff information in association with a staff ID for identifying each medical staff such as a doctor, a nurse, and clerical staff. In the staff information, the name of the medical staff, a medical department to which the medical staff belongs, and the like are recorded. The database 11 also stores and manages patient information in association with a patient ID for identifying each patient. In the patient information, the name, the gender, the age, and the like of the patient are recorded. Further, the database 11 stores and manages document data of each patient in association with a patient ID of the patient. The document management server 10 registers document data transmitted from the terminal device 20 and the sorting processing device 50 into the database 11 in association with a specified patient ID.

FIG. 2 is a diagram illustrating an example of document data stored and managed by the database 11. In FIG. 2, document data associated with a patient with a patient ID "1000101" is illustrated. As illustrated in FIG. 2, the database 11 stores and manages various types of document data in association with a patient ID. As items (document classifications) of the document data, a medical record, an examination report, a medical interview sheet, a referral letter, a medical certificate, an explanation and consent form, and the like are listed. Further, the database 11 stores and manages the document data in units of a date of registration of that document data. For example, FIG. 2 illustrates that the first medical record was registered on Jul. 22, 2015, and the second medical record was registered on Aug. 12, 2015.

The document management server 10 provides information and document data stored and managed by the database 11 in response to a request from the terminal device 20 and the sorting processing device 50. For example, when having received a reference request for document data, which specifies a particular patient ID, from the terminal device 20, the document management server 10 searches document data related to that patient ID from the database 11 and provides corresponding electronic data in a referable manner. Further, when having received an editing operation on the electronic data provided to the terminal device 20, the document management server 10 reflects editing contents of the editing operation on the corresponding electronic data.

The terminal device 20 is, for example, a PC (Personal Computer), operated by medical staff such as a doctor. The terminal device 20 is connected to the printer device 30 and can print paper documents or the like created by a doctor. Although FIG. 1 illustrates a configuration in which the terminal device 20 and the printer device 30 are directly connected to each other, the configuration is not limited thereto. For example, the printer device 30 may be connected to the network N1 to operate as a network printer that can be also used from other devices. The number of the terminal devices 20 is not limited to one, but multiple terminal devices 20 may be used.

At a medical site such as a hospital, a printed paper document is still used together with document data computerized in advance, such as an electronic medical record. For example, a referral letter brought from another medical institution is usually a paper document. Also, a paper document is usually used as an explanation and consent form or the like, that is to be signed by a patient. These paper documents are computerized into document data and registered into the database 11 of the document management server 10, so that document data for each patient can be collectively managed. Therefore, it is necessary to sort and register the computerized document data for each patient.

Accordingly, the information processing system of the present embodiment has a configuration for efficiently performing sorting and registration in association with computerization of paper documents. Specifically, the system performs five processes, that is, a code-symbol issuance process performed before computerization of paper documents, a computerizing process that computerizes the paper documents, a sorting process that sorts the computerized paper documents, a sort-result check process that checks and edits a sort result, and a registration process that performs registration into the document management server 10 (the database 11). Each of these processes is described below.

Code-Symbol Issuance Process

Figure 3:
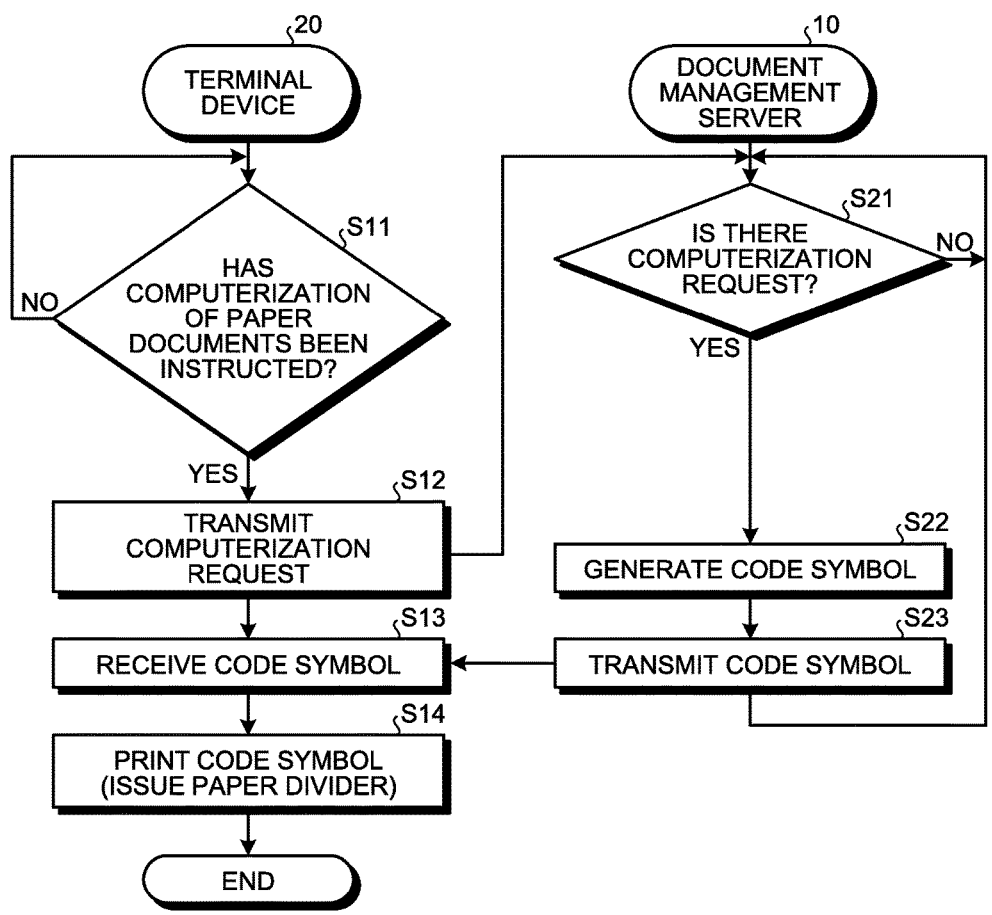
FIG. 3 is a flowchart illustrating an example of a code-symbol issuance process performed by a document management server and a terminal device.

First, the code-symbol issuance process is described with reference to FIG. 3. FIG. 3 is a flowchart illustrating an example of the code-symbol issuance process performed by the document management server 10 and the terminal device 20. The processes in this flowchart are performed by a program that operates on a CPU (Central Processing Unit) included in each of the document management server 10 and the terminal device 20.

First, the terminal device 20 stands by until computerization of a paper document is instructed by medical staff (NO at Step S11). When computerization of a paper document is instructed and a patient ID of a patient related to the paper document is input (YES at Step S11), the terminal device 20 transmits a computerization request including that patient ID to the document management server 10 (Step S12).

At Step S12, when a plurality of patient IDs have been input, the terminal device 20 may transmit the computerization request for each patient ID or may include the plural patient IDs in one computerization request. Further, the medical staff may transmit the medical staff's own staff ID, document-classification information indicating a document classification of a paper divider described later, and bibliographic information related to the paper document, together with the computerization request. It is assumed that it is possible to specify at least a cover sheet and a document other than the cover sheet in the document-classification information.

Meanwhile, the document management server 10 waits for the computerization request transmitted from the terminal device 20 (NO at Step S21). When having received the computerization request from the terminal device 20 (YES at Step S21), the document management server 10 generates a code symbol for each patient ID included in that computerization request, which includes the patient ID (Step S22).

The code symbol described here is a bar code, a two-dimensional code, or the like, and includes a patient ID and legitimate information indicating that the code symbol is a legitimate code symbol. The legitimate information is a fixed number sequence that is predetermined in the system (the medical institute), for example, and it is possible to determine whether the code symbol is a legitimate code symbol issued by the document management server 10 based on the presence or absence of the legitimate information.

Other than the patient ID and the legitimate information described above, the code symbol may include other information. For example, the document management server 10 may include bibliographic information notified together with the computerization request from the terminal device 20, in the code symbol. Further, the document management server 10 may include date-and-time information indicating a date and time of reception of the computerization request in the code symbol. The date-and-time information is preferably recorded by year, month, day, hour, minute, and second so that the date and time of reception is unique. In the present embodiment, first identification information means information encoded into a code symbol (hereinafter, "code information") in whole or in part, and includes at least a patient ID.

Subsequently, the document management server 10 transmits the generated code symbol to the terminal device 20 that is a source of the request (Step S23). The terminal device 20 receives the code symbol as a response to the computerization request following the process at Step S23 (Step S13). The terminal device 20 then controls the printer device 30 to make the printer device 30 print the received code symbol on a predetermined paper sheet, so that a paper divider described later is issued (Step S14), and this process is ended.

The paper sheet on which the code symbol is printed is not specifically limited. For example, the paper sheet may be a blank paper sheet or a paper document separately created by a doctor such as an explanation and consent form. In the former case, it is preferable to specify the document classification of the paper sheet (the paper document) with the code symbol printed thereon as a cover sheet. Further, when the code symbol is printed on the cover sheet, it is preferable to print the patient ID included in that code symbol and patient information such as the name of a patient, corresponding to that patient ID in a visible manner. The patient information can be acquired by performing search using the patient ID as a key from the database 11, for example.

In this manner, a paper sheet with a code symbol printed thereon is issued for each patient related to a paper document to be computerized in the code-symbol issuance process. In the computerizing process described later, the paper sheet with the code symbol printed thereon is inserted between paper documents, so that this paper sheet is used as a paper divider dividing the paper documents for each patient.

Computerizing Process

Next, a computerizing process is described. The computerizing process is performed by making the scanner device 40 illustrated in FIG. 1 read a paper document to be computerized.

The scanner device 40 is a device having a scanner function that optically reads a paper document and converts the paper document to digital image data. The scanner device 40 is realized by, for example, a scanner or an MFP (Multifunction Peripheral) that has a plurality of functions including the scanner function, a printer function, and the like. The scanner device 40 is connected to the sorting processing device 50 and outputs the read image data to the sorting processing device 50. While the scanner device 40 and the sorting processing device 50 are configured to be directly connected to each other in FIG. 1, the configuration is not limited thereto. For example, a configuration may be employed in which the scanner device 40 is connected to the network N1 to output (transmit) the image data to the sorting processing device 50 via the network N1.

Figure 4:
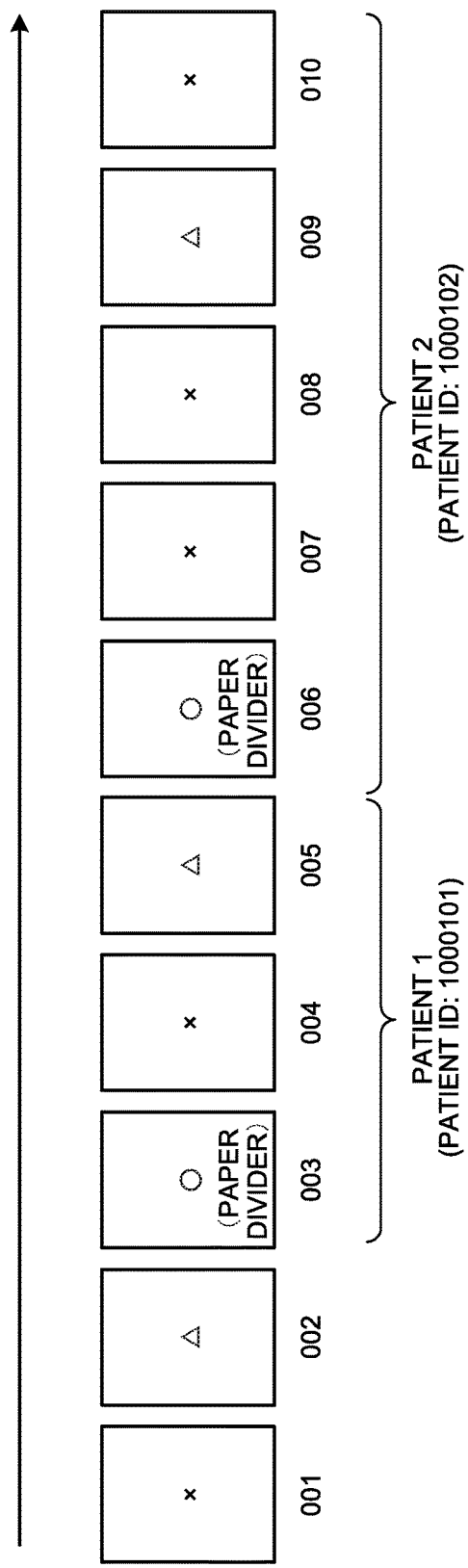
FIG. 4 is a diagram schematically illustrating an example of a reading order of paper documents.

The paper documents to be computerized are read by the scanner device 40 in an order illustrated in FIG. 4, for example. FIG. 4 is a diagram schematically illustrating an example of a reading order of the paper documents. In FIG. 4, a direction indicated with an arrow means that reading is sequentially performed from a paper document of a page 001 to a paper document of a page 010. Further, pages 001, 004, 007, 008, and 010 with cross marks each mean a paper document with no code symbol. Pages 003 and 006 with white circles each mean a paper document with a code symbol including legitimate information (a paper divider).

Pages 002, 005, and 009 with white triangles each mean a paper document with a code symbol including no legitimate information.

Each of the pages 003 and 006 with white circles is located at the first page of a group of paper documents of a patient corresponding to a patient ID included in the code symbol of the corresponding page. That is, it is meant that pages from the page 003 that is the first page with a white circle to the page 005 immediately before the page 006 that is the second page with a white circle are included in a group of paper documents of a patient, and pages from the page 006 with a white circle to the page 010 that is the last page are included in a group of paper documents of another patient. Further, paper documents for which a patient cannot be identified are arranged as the pages 001 and 002 before the page 003 that is the first page with a white circle. In FIG. 4, it is assumed that the pages from the page 003 to the page 005 are paper documents for patient 1 (patient ID: 1000101) and the pages from the page 006 to the page 010 are paper documents for patient 2 (patient ID: 1000102).

Medical staff who performs paper-document reading work collectively sets paper documents for a plurality of patients in the page order illustrated in FIG. 4, in the scanner device 40 to make the scanner device 40 read the documents collectively. The scanner device 40 sequentially reads the set paper documents and outputs read image data to the sorting processing device 50, to perform a computerizing process. The scanner device 40 adds a page number indicating a reading order and date-and-time information indicating the date and time of reading (year, month, day, hour, minute, and second) to a file name of the image data.

Sorting Processing Device

Next, a sorting process, a sort-result check process, and a registration process are described. The sorting process, the sort-result check process, and the registration process are performed by the sorting processing device 50 illustrated in FIG. 1.

The sorting processing device 50 is an information processing device, such as a PC (Personal Computer). The sorting processing device 50 performs a sorting process that acquires image data output from the scanner device 40 and keeps the acquired image data in association with a patient ID, to sort computerized paper documents. Also, the sorting processing device 50 performs a sort-result check process that displays a sort-result check screen indicating the result of the sorting process and changes a sorting destination in accordance with an instruction from a user. Further, the sorting processing device 50 performs a registration process that registers the image data for which sorting has been completed into the document management server 10 (the database 11) as document data.

Figure 5:
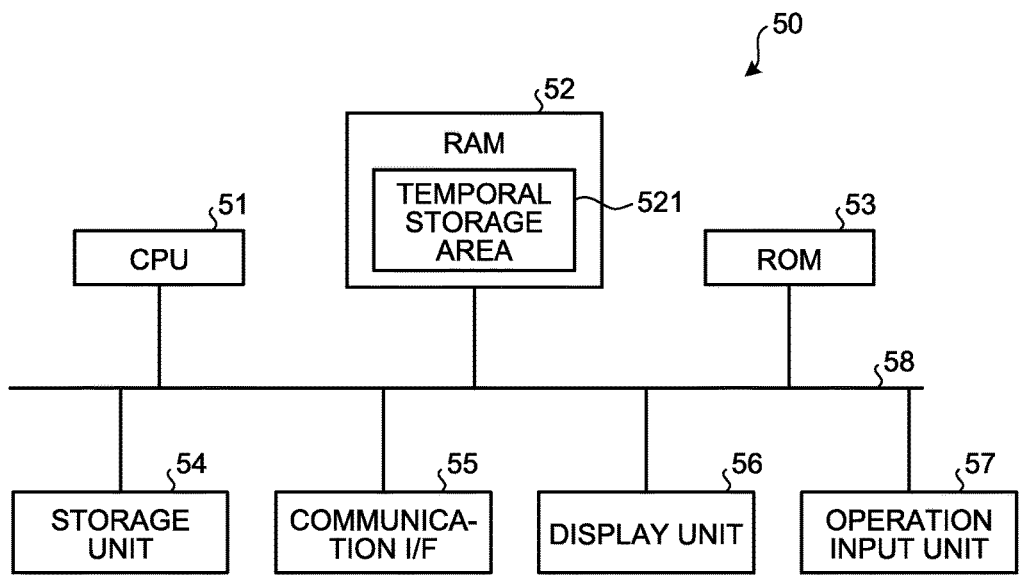
FIG. 5 is a diagram illustrating an example of a hardware configuration of a sorting processing device.

FIG. 5 is a diagram illustrating an example of a hardware configuration of the sorting processing device 50. As illustrated in FIG. 5, the sorting processing device 50 includes a CPU 51, a RAM (Random Access Memory) 52, a ROM (Read Only Memory) 53, a storage unit 54, a communication I/F (Interface) 55, a display unit 56, and an operation input unit 57. These hardware components are mutually connected via a bus 58.

The CPU 51 comprehensively controls the operation of the sorting processing device 50. The CPU 51 executes a program stored in the ROM 53 or the storage unit 54 while using the RAM 52 as a work area, to control the operation of the entire sorting processing device 50. The RAM 52 functions as the work area of the CPU 51. The RAM 52 also functions as a temporal storage area 521 for temporarily storing code information in the sorting process described later. The temporal storage area 521 is configured in such a manner that the temporal storage area 521 is empty (Null) in an initial state and, when new code information is overwritten and saved (stored), only one code information is held therein.

The ROM 53 stores therein various types of programs executed by the CPU 51 and setting information. The storage unit 54 stores therein various types of programs executed by the CPU 51 and setting information. The storage unit 54 also cooperates with a sorting processing unit 514 (see FIG. 6) described later to function as a keeping unit, and stores (keeps) therein sorted image data.

The communication I/F 55 is an interface for communicating with an external device (the document management server 10, the scanner device 40, and the like). The display unit 56 includes a display device and displays various types of information to a user. The operation input unit 57 includes an input device such as a pointing device or a touch panel, and receives an input operation from a user.

Figure 6:
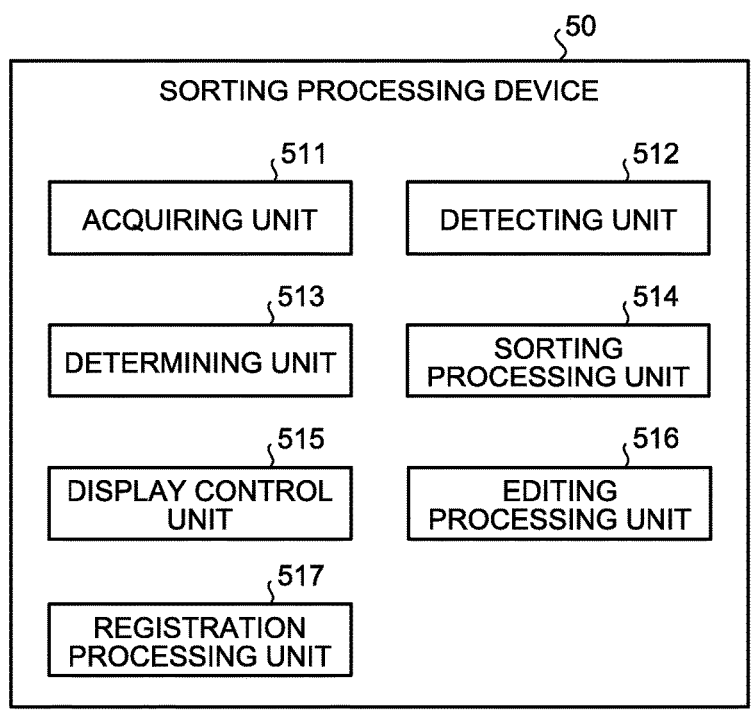
FIG. 6 is a diagram illustrating an example of a functional configuration of the sorting processing device.

FIG. 6 is a diagram illustrating an example of a functional configuration of the sorting processing device 50. As illustrated in FIG. 6, the sorting processing device 50 includes an acquiring unit 511, a detecting unit 512, a determining unit 513, the sorting processing unit 514, a display control unit 515, an editing processing unit 516, and a registration processing unit 517. Each of these components may be partly or entirely realized by software (a program) or may be realized by a hardware circuit.

The acquiring unit 511 acquires image data output from the scanner device 40. The acquiring unit 511 stores the acquired image data in a work area.

The detecting unit 512 corresponds to a detection unit, and detects a code symbol from the image data acquired by the acquiring unit 511. When having detected a code symbol from the image data, the detecting unit 512 decodes the code symbol to read code information such as a patient ID.

The determining unit 513 corresponds to a determination unit, and determines whether legitimate information is included in the code information read by the detecting unit 512. In a case where legitimate information is included in the code information, the determining unit 513 determines that that code information is valid. In a case where no legitimate information is included in the code information, the determining unit 513 determines that that code information is invalid.

The sorting processing unit 514 corresponds to a first sorting unit and a second sorting unit. The sorting processing unit 514 sorts the image data acquired by the acquiring unit 511 based on the patient ID included in the code information determined as being valid by the detecting unit 512. Specifically, the sorting processing unit 514 stores image data acquired before detection of a first code symbol in an unsorted folder and stores image data read after detection of the code symbol in a sorted folder corresponding to code information included in that code symbol. A detailed operation of the sorting processing unit 514 will be described later.

The display control unit 515 generates various types of screens, such as a UI (User Interface) related to an operation of the sorting processing device 50, and makes the display unit 56 display the screens. For example, the display control unit 515 makes the display unit 56 display a sort-result check screen for checking a result of sorting by the sorting processing unit 514.

The editing processing unit 516 is a functional unit corresponding to a changing unit. The editing processing unit 516 cooperates with the display control unit 515 to change a sorting destination or the like of image data in accordance with an operation input via the operation input unit 57.

The registration processing unit 517 is a functional unit corresponding to a registration unit. The registration processing unit 517 transmits image data for which sorting has been completed as document data to the document management server 10 in accordance with an operation input via the operation input unit 57, to perform registration.

Sorting Process

Figure 7:
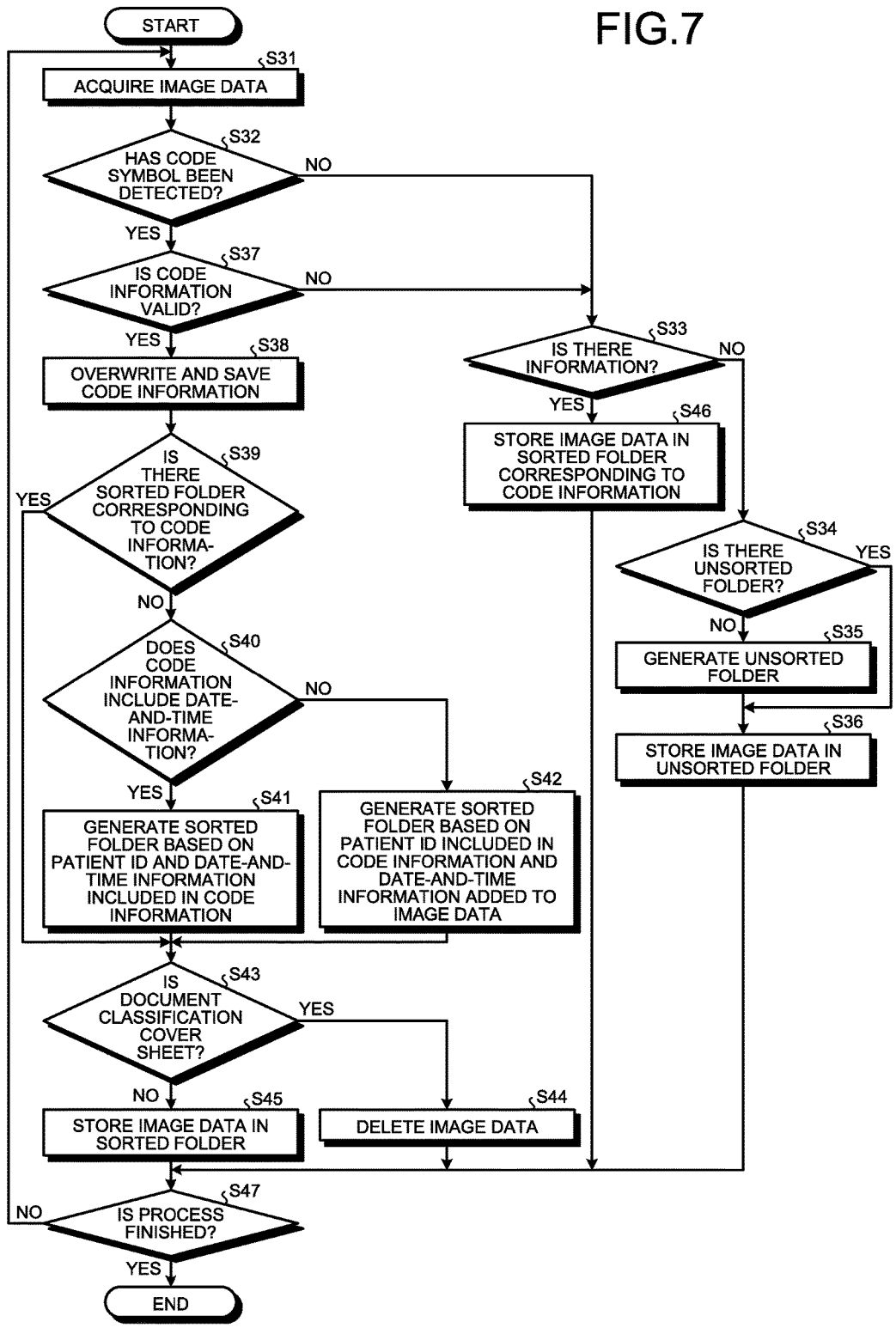
FIG. 7 is a flowchart illustrating an example of a sorting process performed by the sorting processing device.

Next, an operation of the sorting processing device 50 related to a sorting process is described with reference to FIG. 7. FIG. 7 is a flowchart illustrating an example of the sorting process performed by the sorting processing device 50. This process is premised on that reading of paper documents is performed by the scanner device 40 in the order illustrated in FIG. 4.

First, the acquiring unit 511 acquires image data read by the scanner device 40 (Step S31). The detecting unit 512 determines whether a code symbol can be detected from the image data acquired by the acquiring unit 511 (Step S32). When no code symbol is detected (NO at Step S32), the sorting processing unit 514 determines whether code information is saved in the temporal storage area 521 of the RAM 52 (Step S33).

For example, when image data of the page 001 illustrated in FIG. 4 is acquired at Step S31, the detecting unit 512 determines that no code symbol is detected at Step S32 (NO at Step S32) because there is no code symbol in that image data. Also, because the temporal storage area 521 is null at this time, the sorting processing unit 514 determines that no code information is saved at Step S33 (NO at Step S33).

Subsequently, the sorting processing unit 514 determines whether there is an unsorted folder in which image data for which a patient ID is unknown is stored, in the storage unit 54 (Step S34). When there is no unsorted folder (NO at Step S34), the sorting processing unit 514 generates an unsorted folder based on date-and-time information added to the image data (Step S35). The sorting processing unit 514 then stores the image data in the generated unsorted folder (Step S36), and proceeds to Step S47.

For example, there is no unsorted folder in the storage unit 54 at a stage of image data of the page 001 illustrated in FIG. 4. Therefore, the sorting processing unit 514 generates an unsorted folder at Step S35, and stores the image data of the page 001 in the unsorted folder at Step S36.

At the subsequent Step S47, the acquiring unit 511 determines whether there is any next image data (Step S47). When there is next image data (NO at Step S47), the acquiring unit 511 returns to Step S31. When there is no next image data (YES at Step S47), this process is ended. Because there is next image data at the stage of the image data of the page 001, the process returns to Step S31.

When image data of the page 002 illustrated in FIG. 4 is acquired at the subsequent Step S31, the detecting unit 512 determines that a code symbol has been detected at Step S32 (YES at Step S32) because that image data includes the code symbol. In this case, the detecting unit 512 reads code information from the detected code symbol. The determining unit 513 then determines whether the code information read by the detecting unit 512 is valid or invalid (Step S37). When the code information is determined as being invalid (NO at Step S37), the process proceeds to Step S33.

For example, because the code symbol of the image data of the page 002 does not include legitimate information, the determining unit 513 determines the code information is invalid at Step S37. At this time, the temporal storage area 521 is null. Therefore, the sorting processing unit 514 determines that the code information is not stored at Step S33. Also, because the unsorted folder has been already generated, the sorting processing unit 514 determines that there is the unsorted folder in the storage unit 54 at Step S34 (YES at Step S34). In this case, the sorting processing unit 514 stores the image data of the page 002 in the unsorted folder at Step S36 and proceeds to Step S47. At a stage of the image data of the page 002, there is next image data. Therefore, the process returns to Step S31.

At the subsequent Step S31, when image data of the page 003 illustrated in FIG. 4 is acquired, the detecting unit 512 determines that a code symbol has been detected at Step S32 (YES at Step S32) because that image data includes the code symbol. Further, because the code symbol of the image data of the page 003 includes legitimate information, the determining unit 513 determines the code information as being valid at Step S37.

When the code information is determined as being valid by the determining unit 513 (YES at Step S37), the sorting processing unit 514 overwrites and saves that code information in the temporal storage area 521 of the RAM 52 (Step S38). The sorting processing unit 514 then determines whether there is a sorted folder corresponding to the code information saved at Step S38, in the storage unit 54 (Step S39). Here, a sorted folder corresponding to code information means a sorted folder generated at Step S41 or S42 described later with regard to that code information.

When there is no sorted folder corresponding to the code information (NO at Step S39), the sorting processing unit 514 proceeds to Step S40. When there is a sorted folder corresponding to the code information (YES at Step S39), this fact means that the same code symbol has been read a plurality of times. In this case, the sorting processing unit 514 proceeds to Step S43. At this time, it is possible that the sorting processing unit 514 makes the display unit 56 display a notification screen that notifies that the same code symbol has been read a plurality of times.

For example, because legitimate information is included in the code symbol of the image data of the page 003, the determining unit 513 determines that the code information is valid at Step S37. Further, the sorting processing unit 514 overwrites and saves the code information read from the code symbol in the temporal storage area 521 at Step S38. Furthermore, because there is no sorted folder corresponding to the code information at this time, the sorting processing unit 514 determines that the sorted folder is not present at Step S39.

At the subsequent Step S40, the sorting processing unit 514 determines whether date-and-time information is included in the code information saved at Step S38 (Step S40). When date-and-time information is included in the code information (YES at Step S40), the sorting processing unit 514 generates a sorted folder based on a patient ID and the date-and-time information that are included in the code information (Step S41), and proceeds to Step S43. On the other hand, when no date-and-time information is included in the code information (NO at Step S40), the sorting processing unit 514 generates a sorted folder based on a patient ID included in the code information and date-and-time information added to the image data (Step S42), and proceeds to Step S43.

Subsequently, the sorting processing unit 514 determines whether a document classification is a cover sheet based on document-classification information included in the code information (Step S43). When the document classification is a cover sheet (YES at Step S43), the sorting processing unit 514 deletes the image data to exclude the image data from objects to be sorted (Step S44), and proceeds to Step S47. Here, because the cover sheet is a paper sheet (a paper document) on which only information related to a code symbol is printed, it is possible to save the effort of, for example, removing the cover sheet later by excluding the cover sheet from the objects to be sorted at Step S44. A configuration may be employed in which the image data may be prevented from being stored in the sorted folder while the image data is held, to exclude the image data from the objects to be sorted.

When the document classification is other than the cover sheet (NO at Step S43), the sorting processing unit 514 stores the image data in the sorted folder generated at Step S41 or S42 (Step S45), and proceeds to Step S47. At the stage of the image data of the page 003, there is next image data, and therefore the process returns to Step S31.

At the subsequent Step S31, when image data of the page 004 illustrated in FIG. 4 is acquired, the detecting unit 512 determines that a code symbol has been detected at Step S32 because there is a code symbol in that image data. Further, because legitimate information is not included in the code symbol of the image data of the page 003, the determining unit 513 determines that code information is invalid at Step S37. At this time, the code information is saved in the temporal storage area 521, and therefore the sorting processing unit 514 determines that the code information is saved at Step S33.

When having determined that the code information is saved at Step S33 (YES at Step S33), the sorting processing unit 514 stores the image data in a sorted folder corresponding to that code information (Step S46) and proceeds to Step S47.

That is, the image data of the page 004 is stored in the sorted folder generated during processing of the image data of the page 003. Also, as for image data of the page 005, the process proceeds to Step S46 via a procedure of YES at Step S32→NO at Step S37→YES at Step S33, so that the image data of the page 005 is stored in the sorted folder generated during processing of the image data of the page 003, as with the image data of the page 004.

Further, when image data of the page 006 illustrated in FIG. 4 is acquired at the subsequent Step S31, the process proceeds to Step S38 via a procedure of YES at Step S32→YES at Step S37. In this case, the sorting processing unit 514 overwrites and saves code information read from a code symbol of the page 006 in the temporal storage area 521 at Step S38, and generates a sorted folder based on that code information, at Step S41 or Step S42. Subsequently, the sorting processing unit 514 stores the image data of the page 006 in the generated sorted folder when the document classification of the page 006 is other than a cover sheet. Further, the sorting processing unit 514 stores respective image data of the pages 007 to 010 sequentially acquired at Step S31 in the sorted folder generated during processing of the image data of the page 006, as with the respective image data of the pages 004 and 005.

Figure 8:
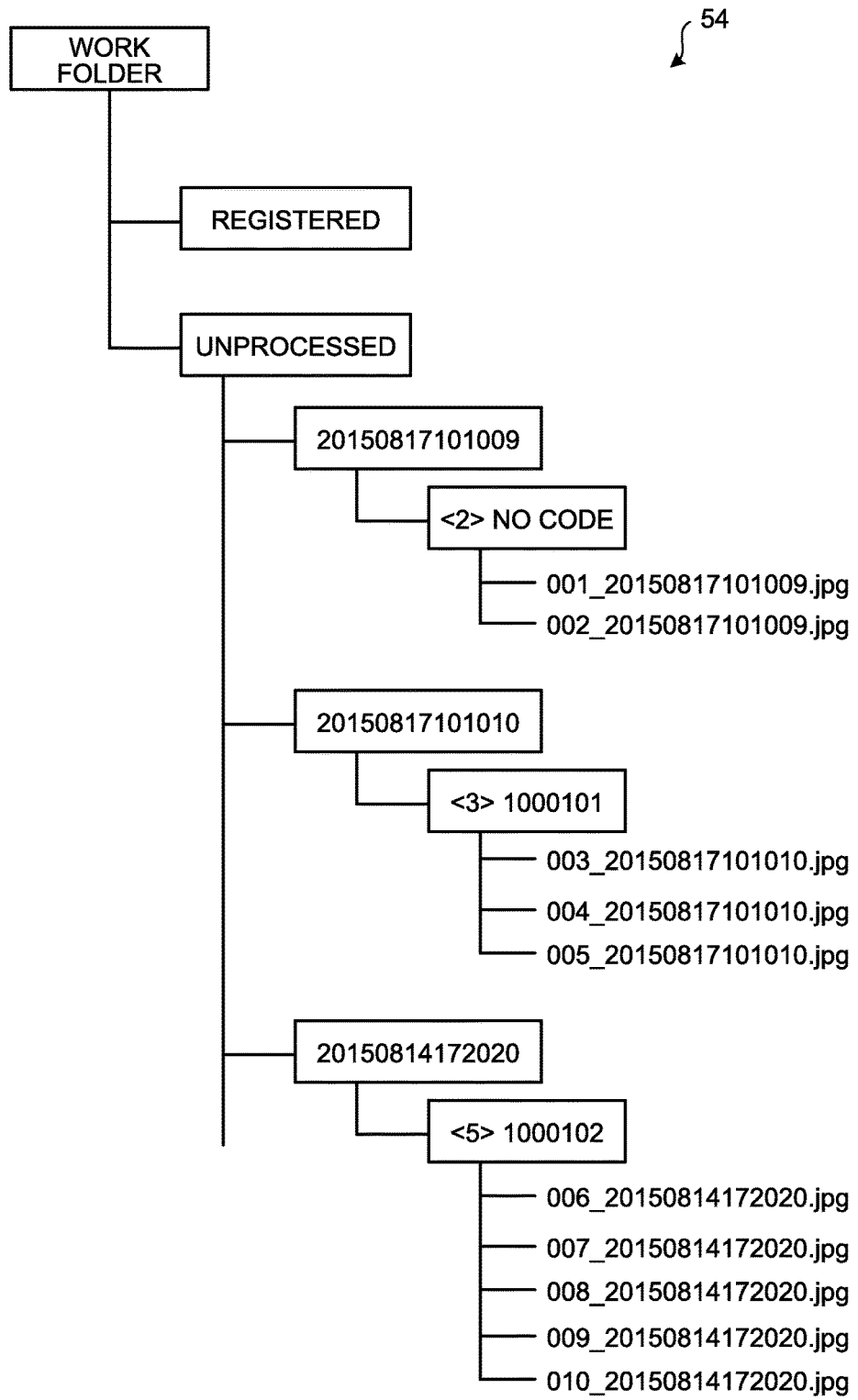
FIG. 8 is a diagram illustrating an example of a folder structure of a storage unit related to storage and management of image data.

A folder (directory) structure of the storage unit 54 related to storage and management of image data is described with reference to FIG. 8. FIG. 8 is a diagram illustrating an example of the folder structure of the storage unit 54 related to storage and management of image data.

As illustrated in FIG. 8, the storage unit 54 has two sub-folders of an "unprocessed" folder and a "registered" folder a root folder of which is a "work folder". The unprocessed folder is an area in which image data before being registered is stored, and the registered folder is an area in which registered image data is stored.

In the unprocessed folder, an unsorted folder described above corresponds to a pair of a date-and-time folder and a no-code folder, and specifically corresponds to a pair of a date-and-time folder with a folder name of "20150817101009" and a no-code folder stored in that date-and-time folder. The file name of the unsorted folder corresponds to second identification information. The unsorted folder is not limited to the example illustrated in FIG. 8, but may be a no-code folder arranged directly under the unprocessed folder, for example.

Also, in the unprocessed folder, the sorted folder described above corresponds to a pair of a date-and-time folder and a patient-ID folder, and specifically corresponds to a pair of a date-and-time folder with a folder name of "20150817101010" and a patient-ID folder with a folder name of a patient ID "1000101" stored in that date-and-time folder. Further, the sorted folder corresponds to a pair of a date-and-time folder with a folder name of "20150814172020" and a patient-ID folder with a folder name of a patient ID "1000102" stored in that date-and-time folder.

Respective image data sorted by the sorting process are stored in the unsorted folder and the sorted folder. For example, respective image data of the pages 001 and 002 illustrated in FIG. 4 are stored in the no-code folder in the "20150817101009" folder. Further, respective image data of the pages 003 to 005 illustrated in FIG. 4 are stored in the "1000101" folder in the "20150817101010" folder. Furthermore, respective image data of the pages 006 to 010 illustrated in FIG. 4 are stored in the "1000102" folder in the "20150814172020" folder. That is, the storage unit 54 stores and manages image data in association with a patient ID via the sorted folder.

In a case where date-and-time information included in a file name of image data and date-and-time information included in a folder name of a date-and-time folder are different from each other, this fact means that the date-and-time folder is generated using date-and-time information included in a code symbol (code information). Further, "<a numerical value>" added to a folder name of a no-code folder or a patient-ID folder means the number of pieces of image data stored in that folder.

In this manner, the sorting processing device 50 sorts image data with no code symbol and image data with invalid code information based on code information (a patient ID) included in a legitimate code symbol in the sorting process. Therefore, even in a case where a paper document including a code symbol (code information) and a paper document with no code symbol are mixed, it is possible to efficiently sort electronic data of these paper documents.

Sort-Result Check Process

Figure 9:
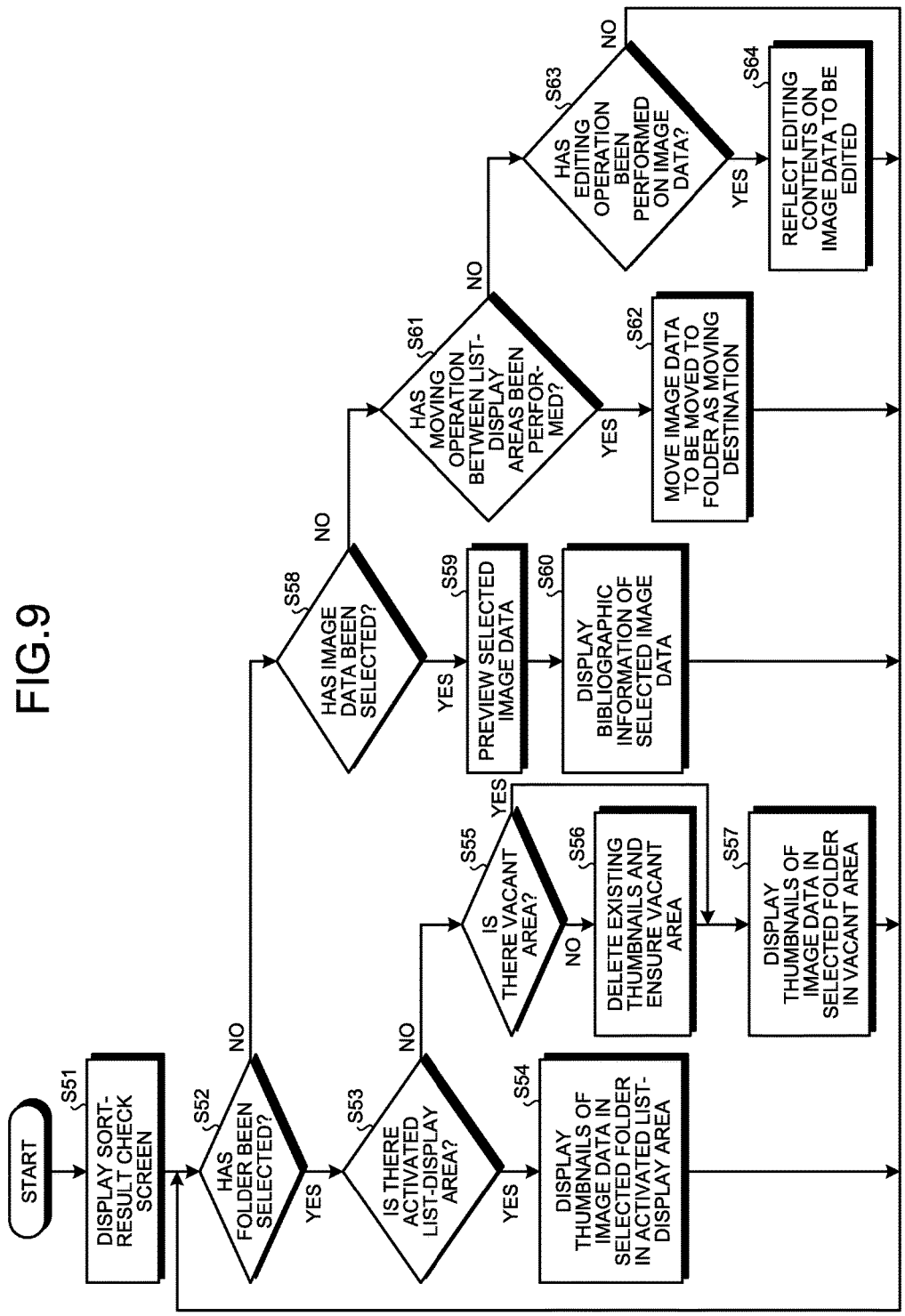
FIG. 9 is a flowchart illustrating an example of a sort-result check process performed by the sorting processing device.

Next, an operation of the sorting processing device 50 related to a sort-result check process is described with reference to FIGS. 9 to 17. FIG. 9 is a flowchart illustrating an example of the sort-result check process performed by the sorting processing device 50. This process is premised on completion of the sorting process.

Figure 10:
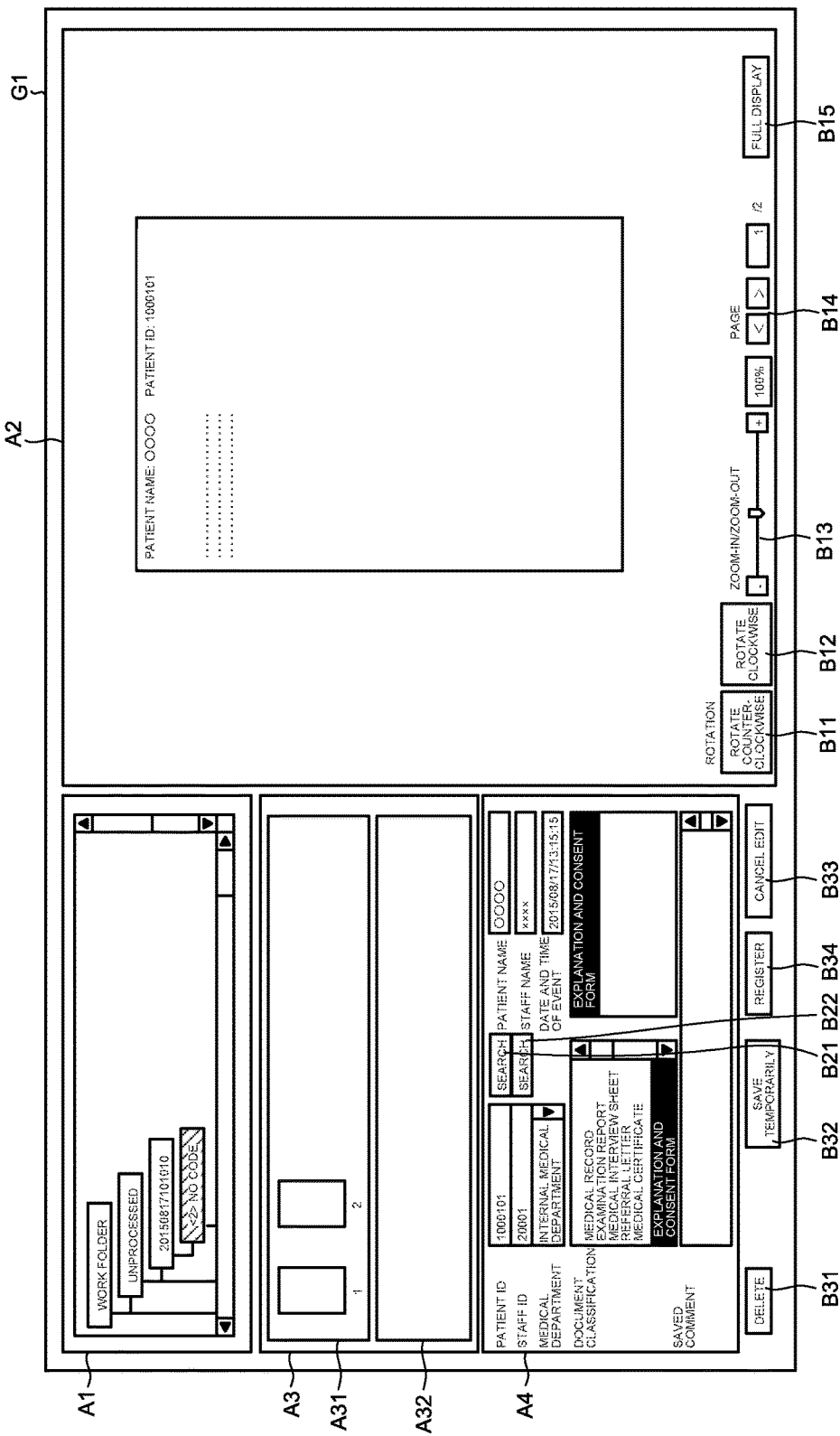
FIG. 10 is a view illustrating an example of a sort-result check screen.

First, when a predetermined operation is performed via the operation input unit 57, the display control unit 515 makes the display unit 56 display a sort-result check screen illustrated in FIG. 10 (Step S51).

FIG. 10 is a view illustrating an example of the sort-result check screen. As illustrated in FIG. 10, a sort-result check screen G1 has four display areas from a first area A1 to a fourth area A4.

The first area A1 corresponds to a first display unit. The first area A1 displays the folder structure of the storage unit 54 illustrated in FIG. 8, for a selecting operation. A user can select intended image data or an intended folder (an unsorted folder or a sorted folder) from the folder structure displayed in the first area A1 via the operation input unit 57.

The second area A2 is an area for previewing image data. The second area A2 also has an operator for operating the previewed image data. For example, the second area A2 has a counterclockwise-rotation button B11 for rotating image data by 90 degrees in a counterclockwise direction and a clockwise-rotation button B12 for rotating image data by 90 degrees in a clockwise direction. The second area A2 also has a zoom-in/zoom-out gauge B13 for changing the display size of image data, a page-feeding button B14 for instructing page feed of image data, and a full display button B15 instructing full display of image data.

The third area A3 corresponds to a second display unit and a reception unit. The third area A3 is an area for displaying thumbnails of image data stored in a folder in a list. The third area A3 has two list-display areas A31 and A32, and displays a plurality of pieces of image data (thumbnails) stored in two folders different from each other such that the plurality of pieces of image data can be compared with each other, using these list-display areas A31 and A32. These list-display areas A31 and A32 can be activated or inactivated by a toggle operation. It is assumed that the list-display areas A31 and A32 are exclusively controlled in such a manner that when one of the two is activated, the other is inactive. Further, a user can perform an operation, such as selection and moving, for the image data (the thumbnails) displayed in the list-display area A31 or A32.

Although the number of the list-display areas arranged in the third area A3 is two in FIG. 10, the number is not limited thereto, and may be three or more. Further, although the list-display areas are arranged in a vertical direction in FIG. 10, the arrangement is not limited thereto, and may be arranged in a horizontal direction.

The fourth area A4 is an area for checking bibliographic information set for a folder or image data or setting (changing) the bibliographic information. As for the bibliographic information, a patient ID, a patient name, a staff ID, a staff name, a medical department, date-and-time information (a date and time of an event), a document classification, comments, and the like can be set for each folder or each image data. Each item of the document classification may be held by the sorting processing device 50 in advance or may be acquired from the document management server 10. Further, input of the bibliographic information is not limited to manual input, but information held by the document management server 10 can be used. Specifically, after a patient ID or a staff ID is input, a search button B21 or B22 is operated. With this operation, the patient name, the staff name, the medical department, or the like corresponding to the patient ID or the staff ID can be acquired from the document management server 10. The patient ID may be automatically input from a folder name of a sorted folder in which the image data is stored.

The sort-result check screen G1 also has an operator related to editing and registration of image data. For example, the sort-result check screen G1 has a delete button B31 for instructing deletion by the folder or by the image data. Further, the sort-result check screen G1 has a save temporarily button B32 for instructing fixing of an editing operation, and a cancel edit button B33 for instructing cancel of an editing operation. Furthermore, the sort-result check screen G1 has a register button B34 for instructing registration into the document management server 10.

Returning to FIG. 9, the display control unit 515 determines whether a folder (an unsorted folder or a sorted folder) has been selected from the first area A1 (Step S52). When a folder has been selected (YES at Step S52), the display control unit 515 determines whether there is an activated list-display area (Step S53). When there is an activated list-display area (YES at Step S53), the display control unit 515 displays thumbnails of image data stored in the selected folder in the activated list-display area (Step S54), and returns to Step S52.

Figure 11:
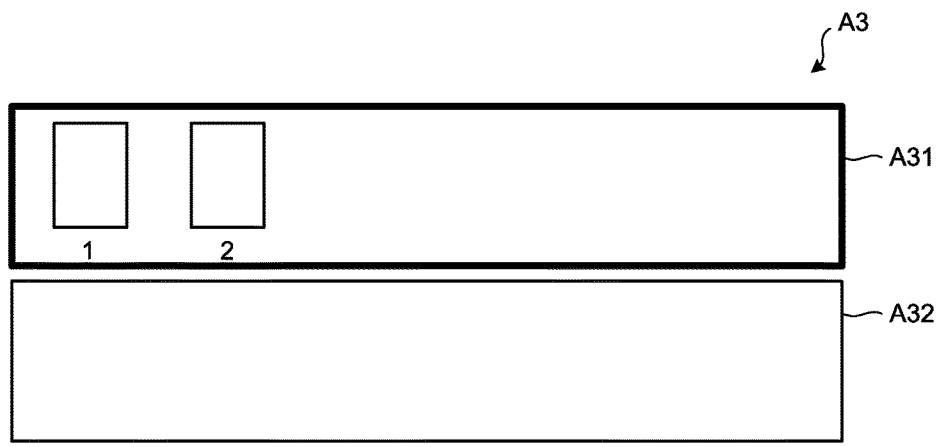
FIG. 11 is an explanatory view of display control of a list-display area.
Figure 12:
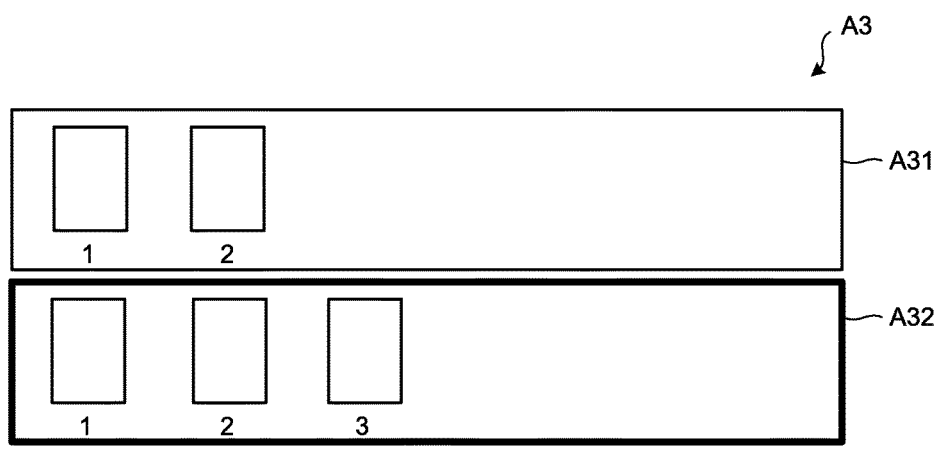
FIG. 12 is an explanatory view of display control of the list-display area.

Display control at Step S54 is described with reference to FIGS. 11 and 12. FIGS. 11 and 12 are explanatory views of display control of the list-display areas A31 and A32. It is assumed here that after the upper list-display area A31 out of the list-display areas A31 and A32 is activated, one folder (one unsorted folder or one sorted folder) is selected. In this case, the display control unit 515 displays thumbnails of image data stored in the selected folder in the list-display area A31, as illustrated in FIG. 11. In FIGS. 11 and 12, the activated list-display area is surrounded by a bold line.

Further, it is assumed that after the lower list-display area A32 is activated in the state illustrated in FIG. 11, another folder different from the folder displayed in the list-display area A31 is selected. In this case, the display control unit 515 displays thumbnails of image data stored in the selected folder in the list-display area A32, as illustrated in FIG. 12.

Returning to FIG. 9, when there is no activated list-display area at Step S53 (NO at Step S53), the display control unit 515 determines whether there is a vacant list-display area in which no thumbnail is displayed (hereinafter, "vacant area") (Step S55). When there is a vacant area (YES at Step S55), the display control unit 515 displays a thumbnail of each image data stored in the selected folder in that vacant area (Step S57), and returns to Step S52.

When there is no vacant area at Step S55 (NO at Step S55), the display control unit 515 deletes existing thumbnails displayed in either one of the list-display areas, to ensure a vacant area (Step S56). Thereafter, the display control unit 515 displays the thumbnail of each image data stored in the selected folder in that vacant area (Step S57), and returns to Step S52.

Figure 13:
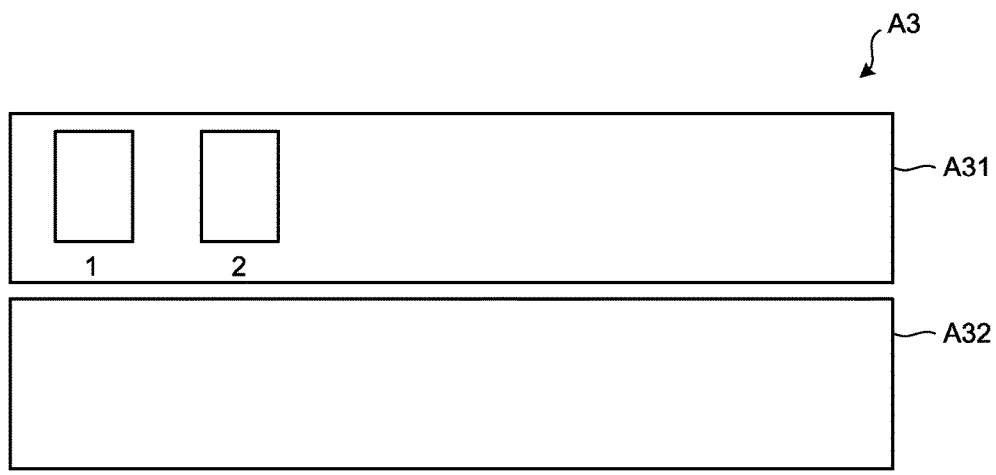
FIG. 13 is an explanatory view of display control of the list-display area.

Display control at Steps S55 to S57 is described with reference to FIGS. 13 to 16. FIGS. 13 to 16 are explanatory views of display control of the list-display areas A31 and A32. First, it is assumed that both the list-display area A31 and the list-display area A32 are vacant and are not activated. When one folder is selected in this state, the display control unit 515 displays a thumbnail of each image data stored in the selected folder in the upper list-display area A31 that is a vacant area, as illustrated in FIG. 13.

Figure 14:
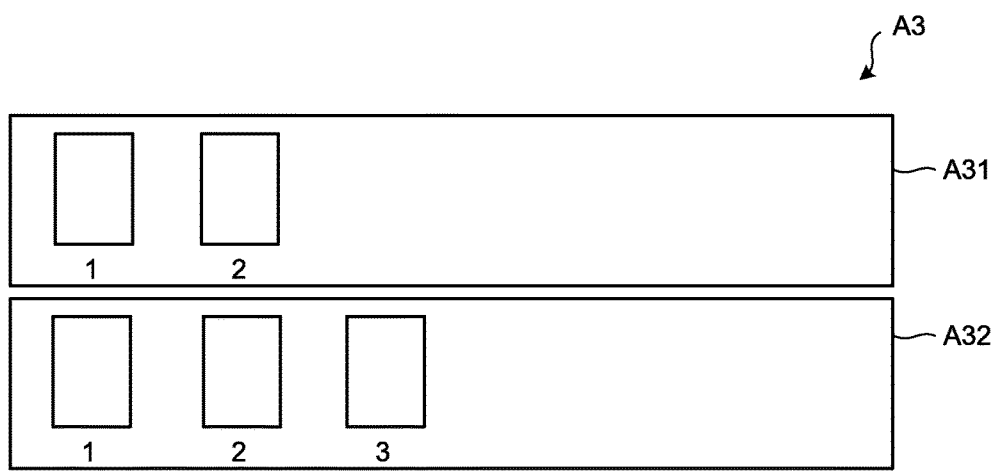
FIG. 14 is an explanatory view of display control of the list-display area.

Further, it is assumed that another folder different from the folder displayed in the list-display area A31 has been selected in the state illustrated in FIG. 13. In this case, the display control unit 515 displays a thumbnail of each image data stored in the selected folder in the lower list-display area A32 that is a vacant area, as illustrated in FIG. 14. Although an example in which the upper list-display area A31 is preferentially used for display is illustrated in FIGS. 13 and 14, a priority order is not limited thereto. The lower list-display area A32 may be preferentially used for display.

Figure 15:
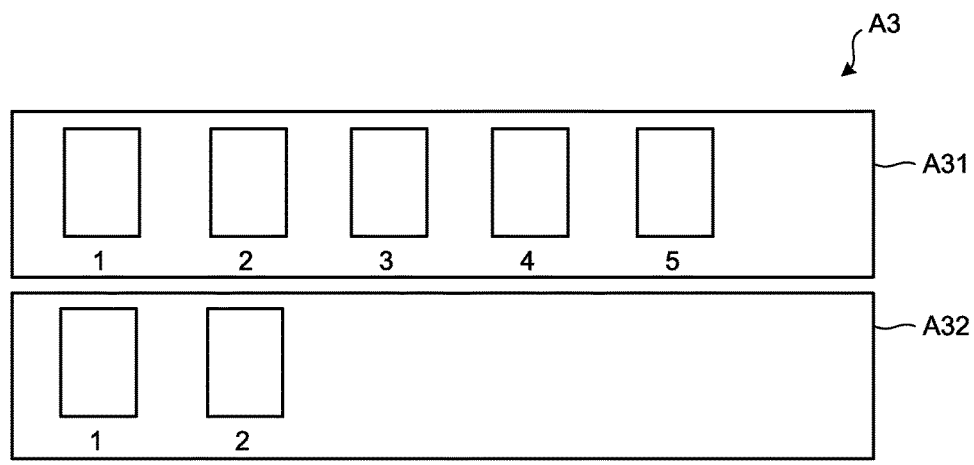
FIG. 15 is an explanatory view of display control of the list-display area.
Figure 16:
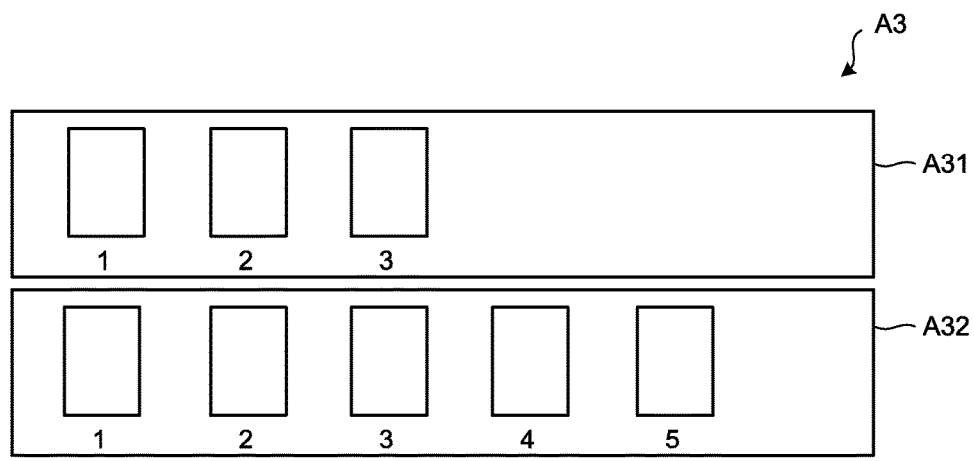
FIG. 16 is an explanatory view of display control of the list-display area.

On the other hand, when there is no vacant area, the display control unit 515 performs display control as illustrated in FIGS. 15 and 16, for example. FIGS. 15 and 16 are explanatory diagrams of display control when it is determined that there is no vacant area at Step S55, and illustrate the third area A3 (the list-display areas A31 and A32) illustrated in FIG. 10 while enlarging the third area A3.

First, it is assumed that both the list-display area A31 and the list-display area A32 display thumbnails and are in an inactive state as illustrated in FIG. 14. Further, it is assumed that another folder different from the folders displayed in the list-display area A31 and the list-display area A32 has been selected in this state. In this case, the display control unit 515 deletes the thumbnails displayed in the lower list-display area A32, and shifts the thumbnails displayed in the upper list-display area A31 to the lower list-display area A32 that has become vacant and displays the thumbnails in the lower list-display area A32. Thereafter, the display control unit 515 displays thumbnails of image data stored in the selected folder in the upper list-display area A31 that has become vacant (see FIG. 15).

Further, it is assumed that another folder different from the folders displayed in the list-display areas A31 and A32 has been selected in the state illustrated in FIG. 15. In this case, the display control unit 515 deletes the thumbnails displayed in the lower list-display area A32 as with the former operation, and shifts the thumbnails displayed in the upper list-display area A31 to the lower list-display area A32 and displays the thumbnails in the lower list-display area A32. Thereafter, the display control unit 515 displays thumbnails of image data stored in the selected folder in the list-display area A31 that has become vacant (see FIG. 16).

In this manner, the display control unit 515 shifts a list-display area in which existing thumbnails are displayed to a predetermined direction, to ensure a vacant area, and displays thumbnails of image data stored in a selected folder in the ensured vacant area. Although an example of performing shift in a direction from the upside to the downside is explained in FIGS. 15 and 16, the direction of shift is not limited thereto, and may be performed in a direction from the downside to the upside. Further, a list-display area that displays thumbnails of a folder a selecting order of which is older, may be preferentially deleted to ensure a vacant area, for example. Furthermore, control may be executed in such a manner that after deletion of thumbnails, the list-display area displaying the existing thumbnails is not shifted.

Returning to FIG. 9, when having received an operation of selecting one image data via the image data displayed in the first area A1 or the thumbnails displayed in the third area A3 (NO at Step S52→YES at Step S58), the display control unit 515 proceeds to a process of Step S59. At Step S59, the display control unit 515 previews the selected image data in the second area A2 (Step S59). In a case where bibliographic information is set for the selected image data or a folder storing that image data, the display control unit 515 displays that bibliographic information in the fourth area A4 (Step S60), and returns to Step S52.

Due to these processes, a user operating the sorting processing device 50 can check the contents of the image data displayed in the second area A2 or the bibliographic information while viewing that image data. Also, the user operating the sorting processing device 50 can perform an editing operation on the image data via the second area A2 or the third area A3, and can set and change the bibliographic information via the fourth area A4, for example.

Figure 17:
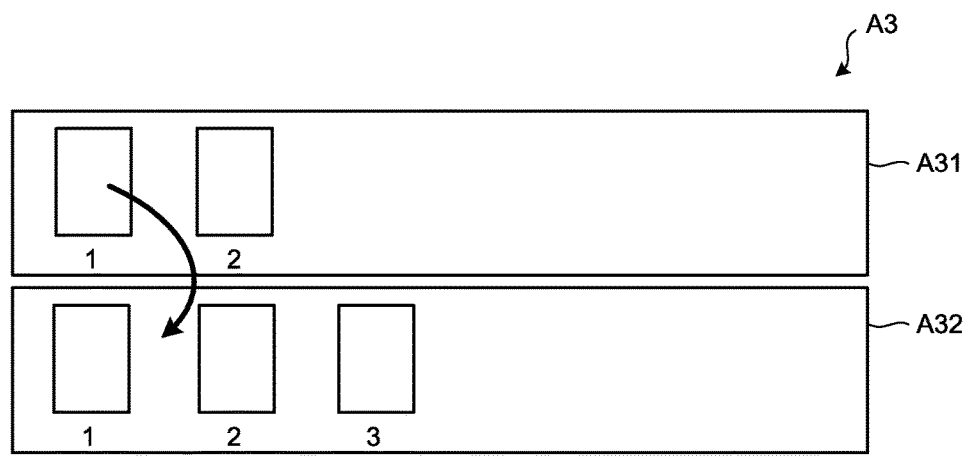
FIG. 17 is an explanatory view of a moving operation of a thumbnail between the list-display areas.

For example, in a case where image data stored in an unsorted folder is sorted to a particular patient, a user performs the following operation. First, as illustrated in FIG. 17, the user selects the unsorted folder (a no-code folder) and a sorted folder (a patient-ID folder) of the patient as a sorting destination, and makes the list-display areas A31 and A32 display thumbnails of these selected folders. FIG. 17 is an explanatory viewm of a moving operation of a thumbnail between the list-display areas.

Subsequently, the user selects a thumbnail to be sorted from one of the list-display areas, that is, the list-display area A31 displaying the thumbnails of the unsorted folder, and moves (drags and drops) the selected thumbnail to the other list-display area, that is, the list-display area A32 displaying thumbnails of the sorted folder. The user then operates the save temporarily button B32 to fix that editing operation.

In FIG. 9, when having received an operation of moving a thumbnail between the list-display areas (NO at Step S51→NO at Step S58→YES at Step S61), the editing processing unit 516 performs a process of Step S62. At Step S62, the editing processing unit 516 moves image data corresponding to the thumbnail that is an object of moving to the sorted folder corresponding to the list-display area that is a destination of moving (Step S62), and returns to Step S52. The number of pieces of image data added to a folder name is updated in association with moving of the image data. Further, in a case where the thumbnail to be moved is inserted between existing thumbnails as illustrated in FIG. 17, a page order after insertion is held.

The moving operation between the list-display areas is not limited to moving between an unsorted folder and a sorted folder. For example, moving from a sorted folder to another sorted folder may be performed. Further, in a case where thumbnails are displayed in one of the list-display areas and the other list-display area is a vacant area, as in the state illustrated in FIG. 13, a thumbnail can be moved to that vacant area. In this case, a folder as the destination of moving is not present. Therefore, the editing processing unit 516 generates a new folder in the unprocessed folder and stores image data that is the object of moving in the new folder. A naming rule of a newly generated folder is not specifically limited. In addition, the folder name and bibliographic information of the newly generated folder can be changed via the first area A1 and the fourth area A4, for example.

Further, a user of the sorting processing device 50 can perform various types of editing operations on image data via the image data previewed in the second area A2 or thumbnails displayed in the list-display area of the third area A3. For example, the user can change a page direction of particular image data by selecting that particular image data (a thumbnail), operating the counterclockwise-rotation button B11 or the clockwise-rotation button B12, and thereafter operating the save temporarily button B32. Further, the user can change a page order of image data by changing the order of corresponding thumbnails displayed in the list-display area and thereafter operating the save temporarily button B32. Furthermore, it is possible to set bibliographic information for particular image data by selecting the particular image data (a thumbnail) and thereafter setting the bibliographic information from the fourth area A4.

In FIG. 9, the editing processing unit 516 performs a process of Step S64 when having received an editing operation for the image data (NO at Step S51→NO at Step S58→NO at Step S61→YES at Step S63). At Step S64, the editing processing unit 516 reflects editing contents on the image data to be edited (Step S64), and returns to Step S52.

For example, when having received an operation of the counterclockwise-rotation button B11 or the clockwise-rotation button B12, the editing processing unit 516 changes a page direction of corresponding image data by an angle corresponding to the operation contents. Also, when having received an operation of changing a display order of thumbnails, the editing processing unit 516 holds the page order after being changed. Further, when bibliographic information has been set, the editing processing unit 516 holds the bibliographic information in association with corresponding image data.

In this manner, the sorting processing device 50 changes the destination of sorting of image data (a storing destination), the page order of image data, and the like in accordance with a user's operation via a sort-result check screen in a sort-result check process. Due to this process, a user of the sorting processing device 50 can easily and efficiently change the destination of sorting, for example, and therefore convenience related to sorting of computerized paper documents can be improved. Further, even in a case where a paper document including a code symbol and a paper document including no code symbol are mixed, the user can edit the destination of sorting while checking thumbnails (image data) of an unsorted folder and a sorted folder displayed in the list-display areas A31 and A32. Therefore, convenience related to sorting of computerized paper documents can be improved.

Registration Process

Figure 18:
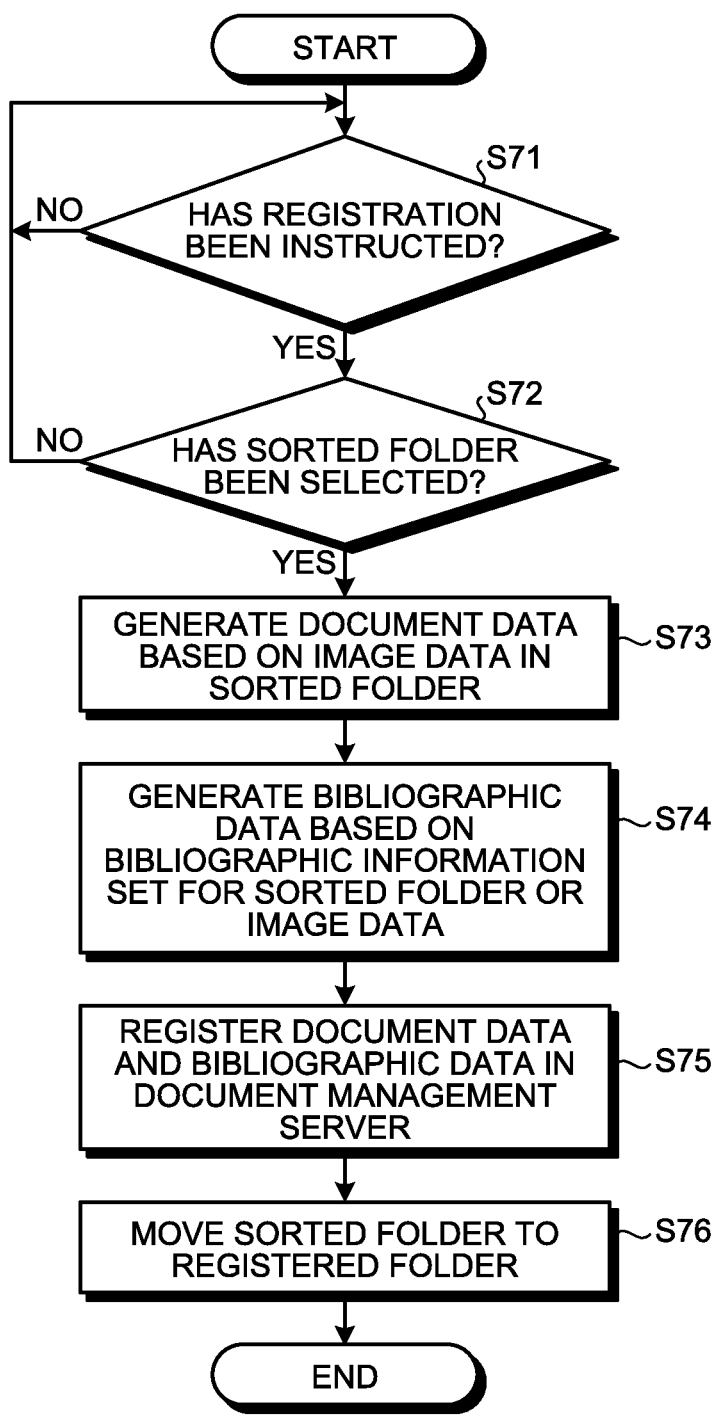
FIG. 18 is a flowchart illustrating an example of a registration process performed by the sorting processing device.

Next, an operation of the sorting processing device 50 related to a registration process is described with reference to FIGS. 18 to 20. FIG. 18 is a flowchart illustrating an example of the registration process performed by the sorting processing device 50. This process is performed in the background of the sort-result check process described above.

First, the registration processing unit 517 stands by until registration is instructed via the operation input unit 57 (NO at Step S71). At this time, when the register button B34 is operated by a user in the sort-result check screen G1 illustrated in FIG. 10, for example, the registration processing unit 517 determines that registration has been instructed (YES at Step S71). At this time, the user of the sorting processing device 50 can select a folder that is an object of registration, by the sorted folder. This selection of the sorted folder may be performed via the first area A1 or may be performed by activating a list-display area displaying thumbnails of the sorted folder.

When registration has been instructed, the registration processing unit 517 determines whether a sorted folder that is the object of registration is selected (Step S72). In a case where a sorted folder is not selected or a case where an unsorted folder is selected (NO at Step S72), the registration processing unit 517 returns to Step S71. At this time, the registration processing unit 517 may display a message that urges the user to select a sorted folder on a sort-result check screen.

At Step S72, in a case where a sorted folder is selected (YES at Step S72), the registration processing unit 517 generates document data for registration based on image data in the selected sorted folder (Step S73). Also, the registration processing unit 517 generates bibliographic data for registration based on bibliographic information set for the selected sorted folder or the image data in that sorted folder (Step S74). Here, the document data is PDF data, for example, and a page order and a page direction of the image data are held. Further, the bibliographic data is a CSV file, for example, and the bibliographic information set for the sorted folder or the bibliographic information set for each page (image data) is held.

Subsequently, the registration processing unit 517 transmits the generated document data and the generated bibliographic data to the document management server 10, to perform registration (Step S75). After completion of registration, the registration processing unit 517 moves the selected sorted folder into a "completed" folder in the storage unit 54 (Step S76), and this process is ended.

Figure 19:
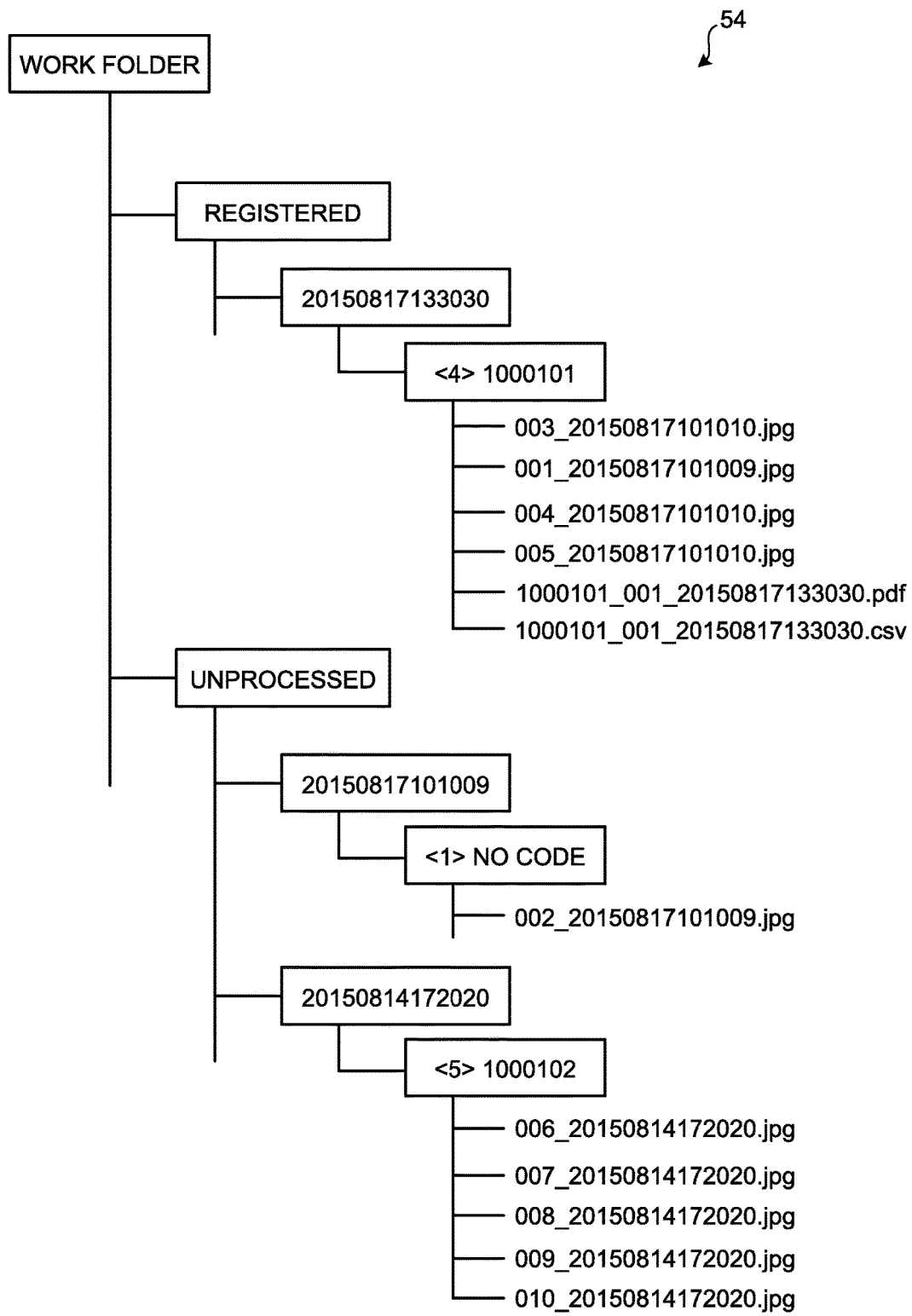
FIG. 19 is a diagram illustrating another example of a folder structure of the storage unit related to storage and management of image data.

FIG. 19 is a diagram illustrating another example of a folder structure of the storage unit 54 related to storage and management of image data. FIG. 19 illustrates a state in which 001_20150817101009.jpg has been moved from an unsorted folder ("20150817101009", a no-code folder) to a sorted folder of "20150817101010"/"1000101" in the state illustrated in FIG. 8 and thereafter registration of this sorted folder is performed. As illustrated in FIG. 19, the registration processing unit 517 moves the sorted folder of "20150817101010"/"1000101" that is an object of registration from an unprocessed folder, to a registered folder, to delete that sorted folder.

Although the file name of the sorted folder (a date-and-time folder) that is the object of registration is changed to the date and time of registration in association with moving to the registered folder in FIG. 19, the file name is not limited thereto. The original file name may be maintained. Further, although the document data (PDF data) and the bibliographic data (CSV file) generated at the time of registration are added into a patient-ID folder, the document data and the bibliographic data may be excluded. In addition, file names of the document data and the bibliographic data and naming rules thereof are not specifically limited. In FIG. 19, an example is illustrated in which the files of the document data and the bibliographic data are named in accordance with a naming rule of [patient ID_medical department code_date and time of registration].

When having received the document data and the bibliographic data from the sorting processing device 50, the document management server 10 registers the document data and the bibliographic data in the database 11 in association with a patient ID included in the file names of the document data and the bibliographic data. Assuming that the document data and the bibliographic data stored in the registered folder in FIG. 19 are an explanation and consent form and these data were registered on Aug. 17, 2015, for example, the document data and the bibliographic data are registered in the database 11 while being associated with a patient ID of 1000101, as illustrated in FIG. 20.

FIG. 20 is a diagram illustrating another example of document data stored and managed by the database 11, corresponding to FIG. 2. Here, an explanation and consent form of Aug. 17, 2015 corresponds to the document data and the bibliographic data described above.

In this manner, it is possible to register image data stored in the sorted folder in units of a sorted folder in the registration process. Further, because a sorted folder for which registration has been completed and a sorted folder for which registration has not been completed are stored in different folders in the storage unit 54, it is possible to easily confirm whether registration has been completed.

Although the embodiment of the present invention has been described above, the embodiment has been presented as illustrative examples, and the scope of the invention is not intended to be limited thereto. The novel embodiment can be also carried out in various other modes, and various omissions, replacements, and changes can be made without departing from the scope of the invention. The present embodiment and modifications thereof are included in the spirit and scope of the invention and are also included in the inventions described in the claims and equivalents thereof.

For example, the programs executed by the sorting processing device 50 according to the embodiment can be recorded in a computer-readable recording medium such as a floppy Disc®, a CD (Compact Disc), a CD-R (Compact Disc-Recordable), a CD-ROM (Compact Disc Read Only Memory), a DVD (Digital Versatile Disc), an SD memory card, and a USB memory (Universal Serial Bus memory), as a file of an installable format or an executable format, and be provided.

Further, the programs executed by the sorting processing device 50 according to the present embodiment can be stored in a computer connected to a network such as the Internet, and be downloaded via the network, to provide the programs.

Figure 21:
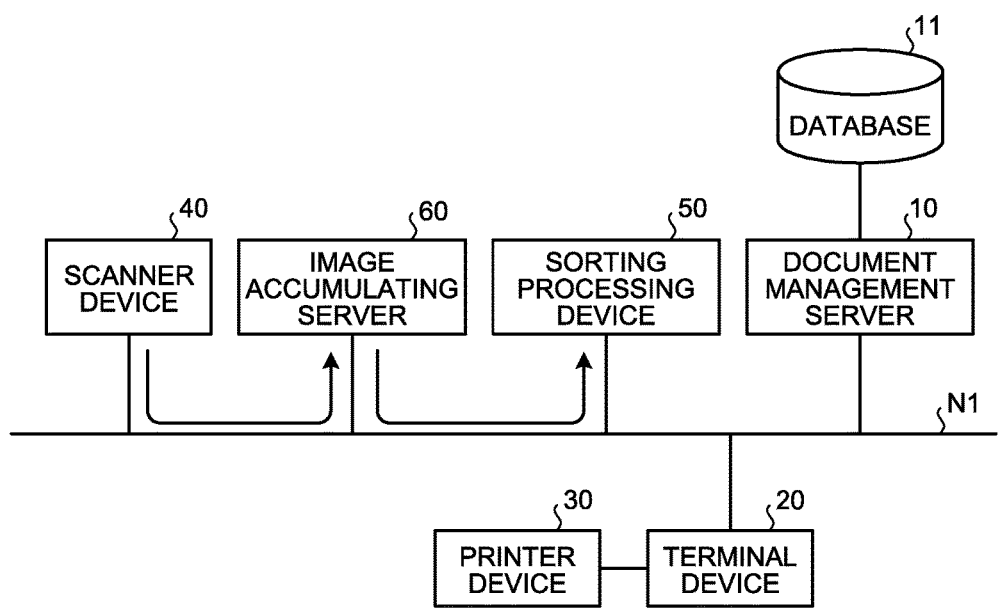
FIG. 21 is a diagram illustrating another example of a configuration of the information processing system according to the present embodiment.

Further, although the sorting processing device 50 is configured to directly acquire image data from the scanner device 40 in the embodiment described above, the configuration is not limited thereto. For example, a configuration may be employed in which an image accumulating server 60 that accumulates image data read by the scanner device 40 is connected to the network N1 and the sorting processing device 50 acquires the image data from this image accumulating server 60, as illustrated in FIG. 21. FIG. 21 is a diagram illustrating another configuration example of the information processing system according to the present embodiment.

Furthermore, although the scanner device 40 and the sorting processing device 50 are separate devices from each other in the embodiment described above, the configuration is not limited thereto, and may be integrated as one device. In addition, a configuration may be employed in which a part of a function provided in the sorting processing device 50 (for example, the detecting unit 512 and the determining unit 513) is provided in the scanner device 40, and the sorting processing device 50 acquires a processing result of a function unit achieved by the scanner device 40, together with image data.

Although a configuration in which a code symbol is printed on a paper sheet and the paper sheet is inserted into existing paper documents is described in the embodiment described above, the configuration is not limited thereto. For example, a configuration may be employed in which a code symbol is printed on a sheet of seal paper or the like and only a portion of the code symbol is affixed to existing paper documents.

In the embodiment described above, a configuration is described in which a paper sheet with a code symbol printed thereon (a paper divider) is inserted as a first page of paper documents of each patient. However, the configuration is not limited thereto. The paper divider may be inserted as a last page of the paper documents of each patient. In a case of employing this configuration, a standard of sorting in the sorting process described above is also changed in accordance with a position of the paper divider. Specifically, image data acquired before detection of a code symbol (legitimate code information) is stored in a sorted folder corresponding to that code information, and image data acquired after detection of a last code symbol (legitimate code information) is stored in an unsorted folder.

More specifically, when code information including legitimate information is read from a code symbol of image data, the sorting processing unit 514 stores that image data and existing image data acquired before that image data in the same sorted folder. Also, when acquisition reaches the last image data, the sorting processing unit 514 stores existing image data that has not been stored in a sorted folder at this time, in an unsorted folder. In this manner, it is possible to sort image data with no code symbol and image data with invalid code information based on code information (a patient ID) included in a legitimate code symbol, as in the embodiment described above.

Further, in the embodiment described above, a configuration is described in which image data with no patient ID is sorted based on a patient ID included in code information read earlier in the sorting process described with reference to FIG. 7. However, the manner of sorting is not limited thereto. Another mode of the sorting process is described below, as a modification of the present embodiment.

Modification

FIG. 22 is a flowchart illustrating another example of the sorting process performed by the sorting processing device 50. In the present modification, a reading order of paper documents is not specifically limited. The reading order may be the same as illustrated in FIG. 4 or may be random.

First, the acquiring unit 511 acquires image data input from the scanner device 40 (Step S81). The detecting unit 512 determines whether a code symbol can be detected from the image data acquired by the acquiring unit 511 (Step S82).

When a code symbol is not detected at Step S82 (NO at Step S82), the sorting processing unit 514 determines whether a folder for storing image data with no code symbol (hereinafter, "no-symbol folder") is present in the storage unit 54 (Step S83). When having determined that a no-symbol folder is not present (NO at Step S83), the sorting processing unit 514 generates a no-symbol folder in an unprocessed folder in the storage unit 54 (Step S84). The sorting processing unit 514 then stores the image data in the generated no-symbol folder (Step S85), and proceeds to Step S98.

At Step S83, when a no-symbol folder is present (YES at Step S83), the sorting processing unit 514 stores the image data in that no-symbol folder (Step S85), and proceeds to Step S98.

On the other hand, when a code symbol has been detected at Step S82 (YES at Step S82), the determining unit 513 determines whether code information read by the detecting unit 512 is valid (Step S86). When the code information has been determined to be invalid by the determining unit 513 (NO at Step S86), the sorting processing unit 514 determines whether a folder for storing image data with invalid code information (hereinafter, "invalid folder") is present in the storage unit 54 (Step S87).

When an invalid folder is not present (NO at Step S87), the sorting processing unit 514 generates an invalid folder in the unprocessed folder in the storage unit 54 (Step S88). Thereafter, the sorting processing unit 514 stores the image data in the generated invalid folder (Step S89), and proceeds to Step S98.

Further, when an invalid folder is present at Step S87 (YES at Step S87), the sorting processing unit 514 stores the image data in that invalid folder (Step S89), and proceeds to Step S98. Steps S90 to S98 are the same as Steps S38 to S47 illustrated in FIG. 7, and therefore the description thereof is omitted.

In this manner, according to the sorting process of the present modification, it is possible to sort image data with no code symbol and image data with non-legitimate code symbol in folders different from each other. Also in this case, it is possible to edit the destination of sorting in units of a folder via a list-display screen of a sort-result check screen, and therefore sorting to patient IDs can be easily and efficiently performed.

According to an embodiment, it is possible to improve convenience related to sorting of computerized paper documents in an environment in which both a paper document including identification information for sorting and a paper document not including the identification information are mixed.

The above-described embodiments are illustrative and do not limit the present invention. Thus, numerous additional modifications and variations are possible in light of the above teachings. For example, at least one element of different illustrative and exemplary embodiments herein may be combined with each other or substituted for each other within the scope of this disclosure and appended claims. Further, features of components of the embodiments, such as the number, the position, and the shape are not limited the embodiments and thus may be preferably set. It is therefore to be understood that within the scope of the appended claims, the disclosure of the present invention may be practiced otherwise than as specifically described herein.

The method steps, processes, or operations described herein are not to be construed as necessarily requiring their performance in the particular order discussed or illustrated, unless specifically identified as an order of performance or clearly identified through the context. It is also to be understood that additional or alternative steps may be employed.

Further, any of the above-described apparatus, devices or units can be implemented as a hardware apparatus, such as a special-purpose circuit or device, or as a hardware/software combination, such as a processor executing a software program.

Further, as described above, any one of the above-described and other methods of the present invention may be embodied in the form of a computer program stored in any kind of storage medium. Examples of storage mediums include, but are not limited to, flexible disk, hard disk, optical discs, magneto-optical discs, magnetic tapes, non-volatile memory, semiconductor memory, read-only-memory (ROM), etc.

Alternatively, any one of the above-described and other methods of the present invention may be implemented by an application specific integrated circuit (ASIC), a digital signal processor (DSP) or a field programmable gate array (FPGA), prepared by interconnecting an appropriate network of conventional component circuits or by a combination thereof with one or more conventional general purpose microprocessors or signal processors programmed accordingly.

Each of the functions of the described embodiments may be implemented by one or more processing circuits or circuitry. Processing circuitry includes a programmed processor, as a processor includes circuitry. A processing circuit also includes devices such as an application specific integrated circuit (ASIC), digital signal processor (DSP), field programmable gate array (FPGA) and conventional circuit components arranged to perform the recited functions.

What is claimed is:

1. An information processing device configured to process image data, comprising:
    a memory including computer readable instructions; and
    a processor, configured to execute the computer readable instructions to
        control storage of image data of a document, in association with first identification information, in a storage device,
        detect whether the first identification information is associated with image data of the document,
        control storage, upon the first identification not being detected as associated with image data, of image data not associated with the first identification information, in the storage device in association with first identification information most recently detected,
        control display of a selection list, from which identification information, including at least the first identification information stored in association with the image data in the storage device, is selectable,
        control display, upon selection of identification information, of a list of image data associated with the selected identification information in a list-display area of a plurality of list-display areas, each of the plurality of list-display areas including a list of displayable image data,
        receive an operation requesting movement of image data specified from the list of image data displayed in the specified list-display area, to another list-display area,
        change, in response to the receiving of the operation in a state in which a list of the image data associated with another piece of identification information selected from the selection list is displayed in the other list-display area, a destination of the specified image data to the other piece of identification information, and
        register the image data, associated with the first identification information, in units of the first identification information in the storage device.

2. The information processing device of claim 1, wherein the at least one processor is configured to control storage of all image data of image data not associated with the first identification information of the document, from detection of the first identification information, until detection of next first identification information by the detection unit, in the storage device in association with the first identification information.

3. The information processing device of claim 1, wherein the at least one processor is further configured to
    determine whether to store the image data of a page including the first identification information in the storage device in association with the first identification information; and
    control storage of the image data from which the first identification information has been detected, in the storage device in association with the first identification information.

4. The information processing device of claim 1, wherein the at least one processor is further configured to
    control storage of image data that is read before image data for which detection of the first identification information has been determined for a first time, of the document, in association with second identification information, wherein the at least one processor is further configured to control display of the selection list from which the identification information including the second identification information is selectable.

5. The information processing device of claim 1, wherein the at least one processor is further configured to
    acquire information in a description format from the image data; and
    determine whether legitimate information indicating a document from which the first identification information is detectable is included in the information in the description format, wherein the at least one processor is further configured to, if the legitimate information is determined to be included, detect the first identification information from the image data corresponding to a document including the legitimate information.

6. The information processing device of claim 1, wherein the at least one processor is further configured to control display of the first identification information registered and the first identification information that is unregistered such that the first identification information registered and the first identification information that is unregistered are distinguishable from one another.

7. The information processing device of claim 1, wherein the at least one processor is further configured to control display of a plurality of list-display areas in a same screen.

8. The information processing device of claim 7, wherein the at least one processor is further configured to control display of two list-display areas in a same screen.

9. The information processing device of claim 7, wherein the at least one processor is further configured to control display of the list-display areas such that the list-display areas are arranged in a vertical direction or a horizontal direction.

10. The information processing device of claim 7, wherein the at least one processor is further configured to, if the identification information is selected in a state in which one of the list-display areas is specified by a user, control display of a list of the image data associated with the identification information in the specified list-display area.

11. The information processing device of claim 7, wherein the at least one processor is further configured to, if the identification information is selected in a state in which none of the list-display areas is specified by a user, specify a vacant display area in which no image data is displayed, of the list-display areas, and control display of a list of the image data associated with the selected identification information in the list-display area.

12. The information processing device of claim 11, wherein the at least one processor is further configured to, if the identification information is selected in a state in which there is no vacant list-display area, control deletion of display in a list-display area of the list-display areas, and control display of a list of the image data associated with the selected identification information in the list-display area.

13. The information processing device of claim 11, wherein the at least one processor is further configured to, if the identification information is selected in a state in which there is no vacant list-display area, control deletion of display in a list-display area which displays a list of the image data associated with identification information a relative selecting order of which is relatively older, of the list-display areas, and control display of a list of the image data associated with the selected identification information in the list-display area.

14. The information processing device of claim 1, wherein
the first, identification information is added to the document while being encoded into a code symbol, and
the detection unit is configured to detect the first identification information from the code symbol acquired from the image data of the document.

15. An information processing system comprising:
an information processing device configured to process image data; and
a document management device configured to manage the image data, the image processing system including:
a memory including computer readable instructions; and
a processor, configured to execute the computer readable instructions to
control storage of image data of a document, in association with first identification information, in a storage device,
detect whether the first identification information is associated with image data of the document,
control storage, upon the first identification not being detected as associated with image data, of image data not associated with the first identification information, in the storage device in association with first identification information most recently detected,
control display of a selection list, from which identification information, including at least the first identification information stored in association with the image data in the storage device, is selectable,
control display, upon selection of identification information, of a list of image data associated with the selected identification information in a list-display area of a plurality of list-display areas, each of the plurality of list-display areas including a list of displayable image data,
receive an operation requesting movement of image data specified from the list of image data displayed in the specified list-display area, to another list-display area,
change, in response to the receiving of the operation in a state in which a list of the image data associated with another piece of identification information selected from the selection list is displayed in the other list-display area, a destination of the specified image data to the other piece of identification information, and
register the image data, associated with the first identification information, in units of the first identification information in the storage device.

16. An information processing method for processing image data of a document, comprising:
controlling storage of image data of a document, in association with first identification information, in a storage device,
detecting whether first identification information is associated with image data of the document;
controlling storage, upon the first identification information not being detected in the detecting, of image data not associated with the first identification information, in the storage device in association with the first identification information most recently detected;
displaying a selection list, from which identification information including at least the first identification information stored in association with the image data in the storage device, is selectable;
displaying, upon selecting the identification information, a list of the image data associated with the selected identification information in a list-display area of a plurality of list-display areas, each of the plurality of list-display areas including a list of displayable image data;
receiving an operation requesting movement of image data specified from the list of image data displayed in the specified list-display area, to another list-display area;
changing, in response to the receiving of the operation in a state in which a list of the image data associated with another piece of identification information selected from the selection list is displayed in the other list-display area, a destination of the specified image data to the other piece of identification information; and
registering the image data, associated with the first identification information, in units of the first identification information in the storage device.

* * * * *